United States Patent [19]

Grue-Sorensen et al.

[11] Patent Number: 4,945,098
[45] Date of Patent: Jul. 31, 1990

[54] NOVEL PROPANE-1,3-DIOL DERIVATIVES AND USE

[75] Inventors: Gunnar Grue-Sørensen, Ølstykke; Christian K. Nielsen, Værløse, both of Denmark

[73] Assignee: Leo Pharmaceutical Products Ltd. A/S (Lovens Kemiske Fabrik Produktionsaktieselskab), Ballerup, Denmark

[21] Appl. No.: 78,525

[22] PCT Filed: Nov. 20, 1986

[86] PCT No.: PCT/DK86/00128
§ 371 Date: Jul. 10, 1987
§ 102(e) Date: Jul. 10, 1987

[87] PCT Pub. No.: WO87/03281
PCT Pub. Date: Jun. 4, 1987

[30] Foreign Application Priority Data

Nov. 25, 1985 [GB] United Kingdom ............ 8528959

[51] Int. Cl.⁵ .................. C07D 275/02; A61K 31/41
[52] U.S. Cl. .................. 514/365; 548/204; 548/236; 548/341; 546/335; 546/341; 546/174; 546/175; 546/145; 546/146; 546/147; 544/224; 544/336; 544/335; 514/357; 514/358; 514/255; 514/256; 514/247; 514/374; 514/399
[58] Field of Search ............ 548/236, 204, 341; 514/365, 374, 399, 357, 358, 255, 256, 247; 546/145, 146, 147, 335, 341, 174, 175

[56] References Cited

U.S. PATENT DOCUMENTS 4,731,373 3/1988 Barner et al. .......... 548/204

FOREIGN PATENT DOCUMENTS 0142333 5/1985 European Pat. Off. .
0146258 6/1985 European Pat. Off. .

*Primary Examiner*—Jane T. Fan
*Attorney, Agent, or Firm*—Cushman, Darby & Cushman

[57] ABSTRACT

A derivative of 2-methylenepropane-1,3-diol of the general formula I

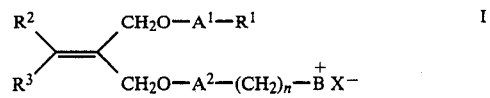

where $O-A^1$ and $O-A^2$, which can be the same or different, each represents $O$, $O-C(O)$, $O-C(O)NH$, $O-C(S)NH$ or $O-C(O)O$, $R^1$ represents an alkyl or alkenyl group of 10-22 carbon atoms, n is an integer from 1 to 11, $B^+$ represents a quaternary ammonium group, either $N^+R^4R^5R^6$, or $N^+(Het)$, where $R^4$, $R^5$ and $R^6$ are similar or different alkyl groups of 1-4 carbon atoms, or two or all of $R^4$, $R^5$ and $R^6$ may be incorporated into a cyclic or bicyclic structure, which may contain additional hetero atoms; $X^-$ means the anion of a pharmceutically acceptable inorganic or organic acid; and $R^2$ and $R^3$ are the same or different, and represent hydrogen or alkl groups of 1-4 carbon atoms.

The present compounds have been shown to possess a PAF antagonistic effect and an inhibitory effect on the growth of tumor cells, and are thus valuable in the human and veterinary practice as platelet aggregation inhibitors, anti-thrombotic agents, anti-asthmatic agents, anti-allergic agents, anti-inflammatory agents, anti-hypotensive agents, anti-ulcer agents, anti-psoriatic agents, anti-graft rejection agents, anti-conception agents and anti-tumor agents.

12 Claims, No Drawings

NOVEL PROPANE-1,3-DIOL DERIVATIVES AND USE

The present invention relates to hitherto unknown derivatives of 2-methylenepropane-1,3-diol, to methods for producing said new derivatives, to pharmaceutical compositions containing said new derivatives, to dosage units of said compositions, and to methods for treating patients using said new derivatives.

Recently, a lipid chemical mediator which plays an important role in platelet aggregation and in allergic, asthmatic, inflammatory and hypotensive reactions, was identified. It was named platelet activating factor (PAF), and it turned out to be a mixture of two alkyl-phospholipids:

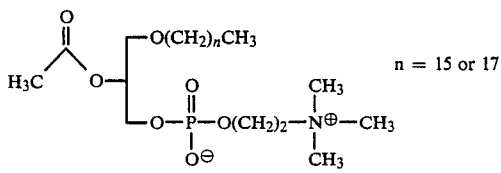

Compounds having PAF antagonistic effect (inhibitory effect on PAF activity) are potentially useful as platelet agregation inhibitors, anti-thrombotic, anti-allergic, anti-asthmatic, anti-inflammatory, anti-hypotensive, anti-ulcer, anti-psoriatic, anti-graft rejection and/or anti-conception agents (cf. D. J. Hanahan, *Ann. Rev. Biochem.*, 55, (1986), 483–509. Abstracts from "Second International Conference on Platelet-Activating Factor and Structurally Related Alkyl Ether Lipids", Gatlinburg, Tenn., U.S.A., Oct. 26–29, 1986).

Thus, investigations have been carried out in order to discover compounds similar to PAF in their chemical structure and possessing a PAF antagonistic effect or having a hypotensive effect like PAF. The results of such investigations have been described e.g. in European Patent Publications Nos. 94586, 109255, 142333, 147768 and 157609 and in German patent application No. 3,307,925. All compounds described in these applications are 1,2,3-trisubstituted propanes with three $sp^3$-hybridized carbon atoms (like PAF):

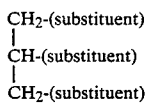

Surprisingly, we have now discovered that the desired PAF antagonistic effect can be obtained with derivatives of 2-methylenepropane-1,3-diol of the general formula I

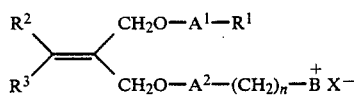

where O—$A^1$ and O—$A^2$, which can be the same or different, each represents O, O—C(O), O—C(O)NH, O—C(S)NH or O—C(O)O, $R^1$ represents an alkyl or alkenyl group of 10–22 carbon atoms, n is an integer from 1 to 11, $B^+$ represents a quaternary ammonium group, either $N^+R^4R^5R^6$, or $N^+$(Het), where $R^4$, $R^5$ and $R^6$ are similar or different alkyl groups of 1–4 carbon atoms, or two or all of $R^4$, $R^5$ and $R^6$ may be incorporated into a cyclic or bicyclic structure, which may contain additional hetero atoms, such as 1-azetidinyl, 1-pyrrolidinyl, 1-piperidinyl, 1-hexamethyleneiminyl, 1-imidazolidinyl, 1-piperazinyl, 1-pyrrolyl, 1-imidazolyl, 4-morpholinyl, triethylenediamin-1-io, 1-quinuclidinio, and where —$N^+$(Het) represents an aromatic heterocyclic ring substituent containing at least one nitrogen atom, such as 1-pyridinio, 1-pyridazinio, 1-pyrimidinio, 1-pyrazinio, 3-oxazolio, 3-thiazolio, 1-isoquinolinio, 1-quinolinio, 3-alkyl-1-imidazolio, which may be substituted or unsubstituted; $X^-$ means the anion of a pharmaceutically acceptable inorganic or organic acid, e.g. the anion of an inorganic acid such as hydrochloric acid, hydrobromic acid, hydroiodic acid, sulfuric acid, phosphoric acid, nitric acid, or the anion of an organic acid such as acetic acid, lactic acid, tartaric acid, benzoic acid, citric acid, methanesulfonic acid, ethanesulfonic acid, benzenesulfonic acid, toluenesulfonic acid, isethionic acid, in particular a halogen ion, i.e. chlorine, bromine, iodine ions, or the anions of methanesulfonic acid or p-toluenesulfonic acid; and $R^2$ and $R^3$ are the same or different, and represent hydrogen or alkyl groups of 1–4 carbon atoms.

Preliminary tests seem to indicate that compounds of formula I, in which $R^2=R^3=$ hydrogen, and n is an integer from 4 to 9, have particularly interesting properties.

The expression of an alkyl group or an alkenyl group in the definition of the various symbols in this present specification including claims represents a straight- or branched-chain alkyl or alkenyl group.

Examples of an alkyl group of 10 to 22 carbon atoms represented by $R^1$ in the formula I are decyl, undecyl, dodecyl, tridecyl, tetradecyl, pentadecyl, hexadecyl, heptadecyl, octadecyl, nonadecyl, eicosyl, heneicosyl and docosyl group and isomers thereof; an alkyl group of 13 to 19 carbon atoms is preferred.

Examples of an alkenyl group of 10 to 22 carbon atoms, represented by $R^1$ in the formula I, when $A^1$ represents a single bond, are the groups which have a double bond between two carbon atoms in the alkyl group enumerated above and when $A^1$ is different from a single bond, are the groups which have a double bond between two carbon atoms except the carbon atom adjacent to $A^1$ in the alkyl group enumerated above.

The present compounds have been shown to possess a PAF antagonistic effect and an inhibitory effect on the growth of tumor cells, and are thus valuable in the human and veterinary practice as platelet aggregation inhibitors, anti-thrombotic agents, anti-asthmatic agents, anti-allergic agents, anti-inflammatory agents, anti-hypotensive agents, anti-ulcer agents, anti-psoriatic agents, anti-graft rejection agents, anti-conception agents and anti-tumor agents.

Some of the above effects have been confirmed in animal experiments using standard laboratory tests. Thus, the platelet activating factor antagonistic activity was tested by determination of inhibition of PAF-induced (1) platelet aggregation in platelet rich plasma from rabbits,
(2) bronchoconstriction in guinea pigs and
(3) acute hypotensive activity in rats (1) Platelet rich plasma derived from rabbit blood was stabilized by 90 mM trisodium citrate in an amount of one tenth of the blood volume. The platelet aggregation was carried out at 37° C. in an aggregometer. After a stabilizing period of 2 minutes, the compounds to be tested were added 2 minutes before adding PAF to a final concentration of 30 ng/ml. The $EC_{50}$ values represent the molar concentration of test compounds inhibiting aggregation by 50%. Some of the tested compounds exhibited $EC_{50}$ values $<5\times 10^{-7}M$.

(2) The tested compounds were able in doses of 1-20 mg/kg i.v. to inhibit bronchoconstriction in anaesthetized guinea pigs caused by intravenous injection of PAF (100 ng/kg body weight). The β-adrenergic receptors of the animals were blocked during the experiment by intravenous injections of propranolol (0.1 mg/kg) on animals, muscle-depolarized by suxamethonum (NFN) (1.2 mg/kg i.v.). The bronchoconstriction was measured ad modum Konzett-Rössler. (H. Konzett and R. Rössler, *Arch. Exp. Pathol. Pharmacol.*, 195, (1940), 71-74). Respiration pressure was 8 cm $H_2O$.

(3) Pretreatment of pentobarbital anaesthetized rats with the tested compounds in doses of 0.1-20 mg/kg i.v. were able to inhibit hypotensive blood pressure reactions induced by PAF i.v. (500 ng/kg body weight). The blood pressure was measured by transducers cannulated to arteria carotis.

The present invention relates also to methods for producing the compounds of formula I. They can be produced by reacting a compound having the general formula II

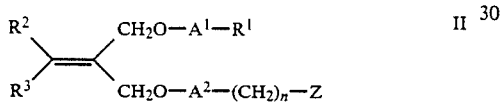

where $A^1$, $A^2$, $R^1$, $R^2$, $R^3$ and n are as defined above and $Z$ is a suitable leaving group, such as chloride, bromide, iodide, benzenesulfonate, toluenesulfonate or methanesulfonate, with a trialkylamine $NR^4R^5R^6$, where $R^4$, $R^5$ and $R^6$ are as defined above, or with a heterocyclic amine N(Het), as defined above, alone or dissolved in a suitable solvent, such as methanol, ethanol, propanol, ethylacetate, methylene chloride, chloroform, ether or tetrahydrofuran or mixtures thereof. When $Z^-$ is a halide, the reaction may be carried out in the presence of a silver salt, AgX, where $X^-$ is different from a halide. Any anion $Z^-$ may be exchanged with another anion $X^-$ by known methods, such as ion exchange chromatography.

The starting material of formula II, where $A^2$ is a single bond, can be produced from a compound of the formula III

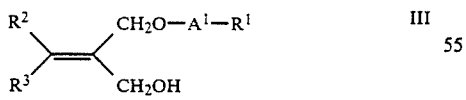

in which $A^1$, $R^1$, $R^2$, and $R^3$ have the above meanings, by deprotonation with a strong base, such as sodium hydride or potassium t-butoxide in a suitable solvent, such as dimethylformamide, dioxane, 1,2-dimethoxyethane or tetrahydrofuran, followed by a reaction with $Y(CH_2)_nZ$, where Z and n have the above meanings and Y is another suitable leaving group, such as chloride, bromide, iodide, benzenesulfonate, toluenesulfonate or methanesulfonate, Y being more reactive than Z or equal to Z.

The starting material of formula II, where $A^2$ is a carbonyl group, can be produced from a compound III by reaction with either (a) $HOOC(CH_2)_nZ$ and dicyclohexylcarbodiimide or
(b) $ClC(O)(CH_2)_nZ$, in which Z and n have the above meanings, both in the presence of a tertiary amine, such as triethylamine, pyridine or 4-dimethylaminopyridine, alone or in an inert solvent, such as ether, methylene chloride or chloroform.

The starting material of the formula II, where $A^2$ is C(O)NH or C(S)NH, can be produced from a compound of formula III by reaction with $OCN(CH_2)_nZ$ or $SCN(CH_2)_nZ$, respectively, n and Z having the above meanings, in the presence of a tertiary amine, such as triethylamine, pyridine or 4-dimethylaminopyridine, alone or in an inert solvent, such as ether, methylene chloride, chloroform or toluene.

The starting material of the formula II, where $A^2$ is C(O)O, can be produced from a compound of formula III by reaction with $ClC(O)O(CH_2)_nZ$, n and Z having the above meanings, in the presence of a tertiary amine, such as triethylamine, pyridine or 4-dimethylaminopyridine, alone or in an inert solvent, such as ether, methylene chloride, chloroform or toluene.

The compounds of the formula III, where $A^1$ is a single bond, can be produced from a compound of formula IV

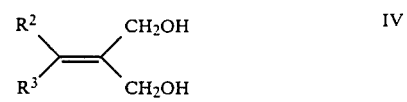

by deprotonation with a strong base, such as sodium hydride or potassium t-butoxide, in a suitable solvent, such as dimethylformamide, dioxane, 1,2-dimethoxyethane or tetrahydrofuran, followed by reaction with $R^1Y$, where $R^1$ and Y are as defined above.

The compounds of the formula III, where $A^1$ is a carbonyl group, can be produced from a compound of formula IV by reaction with either (a) $HOOCR^1$ and dicyclohexylcarbodiimide or
(b) $ClC(O)R^1$, $R^1$ having the above meanings, both in the presence of a tertiary amine, such as triethylamine, pyridine or 4-dimethylaminopyridine, alone or in an inert solvent, such as ether, methylene chloride or chloroform.

The compounds of the formula III, where $A^1$ is C(O)NH or C(S)NH, can be produced from a compound of formula IV by reaction with $OCNR^1$ or $SCNR^1$, respectively, $R^1$ having the above meanings, in the presence of a tertiary amine, such as triethylamine, pyridine or 4-dimethylaminopyridine, alone or in an inert solvent, such as ether, methylene chloride, chloroform or toluene.

The compounds of the formula III, where $A^2$ is C(O)O, can be produced from a compound of formula IV by reaction with $ClC(O)R^1$, $R^1$ having the above meanings, in the presence of a tertiary amine, such as triethylamine, pyridine or 4-dimethylaminopyridine, alone or in an inert solvent, such as ether, methylene chloride, chloroform or toluene.

The starting material of formula II, where $A^2$ is a single bond, can also be produced from a compound of the formula V

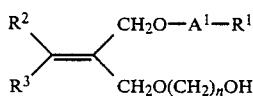

(V)

in which $A^1$, $R^1$, $R^2$, $R^3$, and n have the above meanings, by reaction with a sulfonic acid chloride, such as benzenesulfonyl chloride, toluenesulfonyl chloride or methanesulfonyl chloride in the presence of a tertiary amine, such as triethylamine or pyridine, alone or in an inert solvent, such as ether, methylene chloride or chloroform.

The starting material of formula V can be produced from a compound of the formula VI

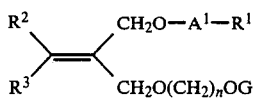

(VI)

in which $A^1$, $R^1$, $R^2$, $R^3$ and n have the above meanings and G represents a suitable alcohol protecting group, such as triphenylmethyl, tetrahydropyranyl or methoxymethyl, by deprotection with a suitable deprotecting agent, such as toluenesulfonic acid, hydrogen chloride, sulfuric acid, acetic acid or acidic ion exchange resin, in a suitable solvent, such as water, methanol or ethanol, alone or mixed with an inert solvent, such as ether, chloroform or methylene chloride.

The compounds of the formula VI, where $A^1$ is a single bond, can be produced from a compound of formula VII

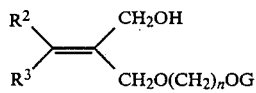

(VII)

in which n and G have the above meanings, by deprotection with a strong base, such as sodium hydride or potassium t-butoxide, in a suitable solvent, such as dimethylformamide, dioxane, 1,2-dimethoxyethane or tetrahydrofuran, followed by reaction with $R^1Y$, where $R^1$ and Y are as defined above.

The compounds of the formula VI, where $A^1$ is a carbonyl group, can be produced from a compound of formula VII by reaction with either (a) $HOOCR^1$ and dicyclohexylcarbodiimide or
(b) $ClC(O)R^1$, $R^1$ having the above meanings, both in the presence of a tertiary amine, such as triethylamine, pyridine or 4-dimethylaminopyridine, alone or in an inert solvent, such as ether, methylene chloride or chloroform.

The compounds of the formula VI, where $A^1$ is $C(O)NH$ or $C(S)NH$, can be produced from a compound of formula VII by reaction with $OCNR^1$ or $SCNR^1$, respectively, $R^1$ having the above meanings, in the presence of a tertiary amine, such as triethylamine, pyridine or 4-dimethylaminopyridine, alone or in an inert solvent, such as ether, methylene chloride, chloroform or toluene.

The compounds of the formula VI, where $A^1$ is $C(O)O$, can be produced from a compound of formula VII by reaction with $ClC(O)R^1$, $R^1$ having the above meanings, in the presence of a tertiary amine, such as triethylamine, pyridine or 4-dimethylaminopyridine, alone or in an inert solvent, such as ether, methylene chloride, chloroform or toluene.

The starting material of formula VII can be produced from a compound of formula IV, by deprotonation with a strong base, such as sodium hydride or potassium t-butoxide, in a suitable solvent, such as dimethylformamide, dioxane, 1,2-dimethoxyethane or tetrahydrofuran, followed by reaction with $Y(CH_2)_nG$, where Y, n, and G are as defined above.

The preparation of compounds of the formula IV is described in the chemical literature. When $R^2$ and $R^3$ are different, the final compounds of formula I may be provided as mixtures of or, after a suitable separation procedure, well-known in the art, as the pure double bond (E and Z) isomers.

It is a further object of the present invention to provide pharmaceutical compositions which are useful in the human and veterinary practice, and which may be used for enteral, parenteral or topical administration.

With this object in view, the compositions of the invention contain as an active component at least one compound of the formula I, together with solid or liquid pharmaceutical carriers and/or diluents.

Furthermore, the compositions may contain other therapeutically active components, such as glucocorticoids, anti-histamines, anticholinergic agents, methyl xanthines, $\beta$-adrenergic agents, salicylates, indomethacin, flufenamate, naproxen, timegadine, gold salts, penicillamine, serum cholesterol-reducing agents, retinoids, zinc salts, and anti-neoplastic agents, which can be appropriately administered together with the present compounds in the treatment of hypotension, cancer, psoriasis and other proliferative skin disorders, asthma, allergy, inflammatory conditions, endotoxin shock, angina pectoris and thrombosis.

In the said compositions, the proportion of therapeutically active material to carrier substance can usually vary between 1% and 95% by weight. The compositions can be worked up to various pharmaceutical forms of presentation, such as tablets, pills, dragees, suppositories, capsules, sustained-release tablets, solutions, suspensions and the like containing the compounds of formula I as atoxic salts, as defined above, mixed with carriers and/or diluents.

Pharmaceutically acceptable, non-toxic, organic or inorganic, solid or liquid carriers and/or diluents can be used to make up compositions containing the present compounds. Gelatine, lactose, starch, magnesium stearate, talc, vegetable and animal fats and oils, gum, polyalkylene glycol, buffers or other known carriers, auxiliary agents and/or diluents for medicaments are all suitable.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compression or moulding the active ingredient optionally with one or more accessory ingredient(s). Compressed tablets may be prepared by compressing, in a suitable machine, the active ingredient in a free-flowing form such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert liquid diluent.

Liquid compositions for oral administration include pharmaceutically acceptable emulsions, solutions, suspensions, syrups and elixirs containing inert diluents commonly used in the art, such as distilled water or ethanol. Besides inert diluents such compositions may also comprise adjuvants such as wetting and suspending agents, and sweetening, flavouring, perfuming and preserving agents.

Formulations for rectal administration may be in the form of a suppository incorporating the active ingredient and a carrier such as cocoa butter, or in the form of an enema.

Formulations suitable for administration to the nose or buccal cavity include powder, self-propelling and spray formulations such as aerosols and atomizers. The formulations, when dispersed, preferably have a particle size in the range of 10 to 100μ.

Such formulations are most preferably in the form of a finely comminuted powder for pulmonary administration from a powder inhalation device or self-propelling powder-dispensing formulations, where the active ingredient, as a finely comminuted powder, may comprise even up to 99.9% w/w of the formulation. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more lower alkyl hydrocarbons or halogenated lower alkyl hydrocarbons or mixtures thereof; chlorinated and fluorinated lower alkyl hydrocarbons are especially preferred. Generally, the propellant constitutes 50 to 99.9% w/w of the formulation whilst the active ingredient constitutes 0.1 to 20% w/w, for example about 2% w/w, of the formulation.

The pharmaceutically acceptable carrier in such self-propelling formulations may include other constituent in addition to the propellant, in particular a surfactant or a solid diluent or both. Surfactants are desirable since they prevent agglomeration of the particles of active ingredient and maintain the active ingredient in suspension. Especially valuable are liquid non-ionic surfactants and solid anionic surfactants or mixtures thereof. Suitable liquid non-ionic surfactants are esters and partial esters of fatty acids with aliphatic polyhydric alcohols, for instance, sorbitan monooleate and sorbitan trioleate, known commercially as "Span 80" (Trade Name) and "Span 85" (Trade Name), respectively. The liquid non-ionic surfactants may constitute from 0.01 up to 20% w/w of the formulation, though preferably it constitutes below 1% w/w of the formulation. Suitable solid anionic surfactants include alkali metal, ammonium and amine salts of dialkyl sulphosuccinate (where the alkyl groups have 4 to 12 carbon atoms). The solid anionic surfactants may constitute from 0.01 up to 20% w/w of the formulation, though preferably below 1% w/w of the composition. Solid diluents may advantageously be incorporated in such self-propelling formulation where the density of the active ingredient differs substantially from the density of the propellant; also, they help to maintain the active ingredient in suspension. The solid diluent is in the form of a fine powder, preferably having a particle size of the same order as that of the particles of the active ingredient. Suitable solid diluents include sodium chloride, sodium sulphate and sugars.

Formuldtions of the present invention may also be in the form of a self-propelling formulation wherein the active ingredient is present in solution. Such self-propelling formulations may comprise the active ingredient, propellant and co-solvent, and advantageously an anti-oxidant stabilizer. The propellant is one or more of these already cited above. Co-solvents are chosen for their solubility in propellant, their ability to dissolve the active ingredient, and for their having the lowest boiling point consistent with these above-mentioned properties. Suitable co-solvents are lower alkyl alcohols and ethers and mixtures thereof. The co-solvent may constitute 5 to 40% w/w of the formulation, though preferably less than 20% w/w of the formulation. Antioxidant stabilizers may be incorporated in such solutions-formulations to inhibit deterioration of the active ingredients and are conveniently alkali metal ascorbates or bisulphites. They are preferably present in an amount of up to 0.25% w/w of the formulation.

Such self-propelling formulations may be prepared by any method known in the art. For example, the active ingredient (either as particles as defined hereinbefore in suspension in a suitable liquid or in up to 20% w/v solution in an acceptable co-solvent, as appropriate) is mixed with any other constituents of a pharmaceutically acceptable carrier. The resulting mixture is cooled, introduced in a suitable cooled container and propellant is added thereto in liquid form; and the container is sealed. Alternatively, such self-propelling formulations may be prepared by mixing the active ingredient either in particles as hereinbefore defined or in 2 to 20% w/v alcohol or aqueous solution as appropriate, together with the remaining constituents of the pharmaceutically acceptable carrier other than the propellant; introducing the resulting mixture, optionally with some propellant, into a suitable container; and injecting the propellant, under pressure, into the container at ambient temperature through a valve which comprises a part of the container and is used to control release of the formulation from it. Desirably, the container is purged by removing air from it at a convenient stage in the preparation of the self-propelling formulation.

A suitable container for a self-propelling formulation is one provided with a manually-operable valve and constructed of aluminium, stainless steel or reinforced glass. The valve should, of course, be one having the desired spray characteristics of particle size as hereinbefore defined. Advantageously, the valve is of the type which delivers a fixed amount of the formulation on the occasion of each operation of the valve, for example, about 50 to 100 microliters of formulation in each delivery.

Formulations of the present invention may also be in the form of an aqueous or dilute alcoholic solution, optionally a sterile solution, of the active ingredient for use in a nebuliser or atomizer, wherein an accelerated air stream is used to produce a fine mist consisting of small droplets of the solution. A buffering agent and a surface active agent may also be included in such a formulation which should also contain a preservative such as methylhydroxybenzoate.

Other formulations suitable for nasal administration include a fine powder having a particle size of 10 to 100 microns which is administered in the manner in which snuff is taken, i.e. by rapid inhalation through the nasal passage from a container of the powder held close up to the nose.

In addition to the aforementioned ingredients, the formulations of this invention may include one or more additional ingredients such as diluents, buffers, flavouring agents, binders, surface active agents, thickeners, lubricants, preservatives, e.g. methylhydroxybenzoate (including anti-oxidants), emulsifying agents and the like.

Preparations according to the present invention for parenteral administration include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, and Polysorbate 80 (registered Trade Mark). These compositions may also include adjuvants such as preserving, wetting, emulsifying and dispersing agents. They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Formulations suitable for intra-articular administration may be in the form of a sterile aqueous preparation of the active ingredient. Liposomal formulations or biodegradable polymer systems may also be used to present the active ingredient for both intra-articular and ophthalmic administration.

Formulations suitable for topical administration include liquid or semi-liquid preparations such as liniments, lotions, applications; oil-in-water or water-in-oil emulsions such as creams, ointments or pastes; or solutions or suspensions such as drops. For example, for ophthalmic administration, the active ingredient may be present in the form of aqueous eye drops as, for example, a 0.1–1.0% solution.

Another object of the invention resides in the selection of a dose of the compounds of the invention and a dosage unit of the compositions of the invention which dose and dosage unit can be administered so that the desired activity is achieved without simultaneous secondary effects. In the human therapy, the present compounds are conveniently administered (to adults) in dosage units of the compositions. By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents, carriers, solvents and/or auxiliary agents.

The dose of the present compounds to be administered depends upon, for example, age, body weight, symptoms, the desired therapeutic effect, the route of administration, and the duration of the treatment.

In the human adult, the doses per person are generally between 1 mg and 2 g, preferably between 20 and 500 mg by oral administration, and between 100 $\mu$g and 200 mg, preferably between 1 and 100 mg by parenteral administration and can be administered up to several times per day, the amounts referring to the content of one or more of the present compounds.

As mentioned above, the doses to be used depend on various conditions. Therefore, there may be cases in which doses greater than the ranges specified above, or lower than the ranges specified above, may be used.

In the form of dosage units, the present compounds may be administered once or more times a day at appropriate intervals, always depending, however, on the condition of the patient, and in accordance with the prescription made by the medical practitioner.

Thus a daily dose will preferably be an amount of from 0.005 to 5 g of a compound of formula I, which conveniently can be divided into several single doses.

In the continuous therapy of patients suffering from chronic diseases, the tablets or capsules are the appropriate form of pharmaceutical preparation, if desired in the form of sustained-release formulations.

In the veterinary practice the above pharmaceutical compositions may also be used, preferably in the form of dosage units containing from 5 mg up to 25 g of the compound of formula I.

Still another object of the invention is to provide a method of treating patients, the method comprising administering to adult patients in need of treatment an effective amount of a compound of formula I, preferably, in the form of the dosage unit aforesaid. The compounds of formula I are typically administered in amounts of 0.1–100 mg/kg body weight of the patient/day.

In the treatment of patients, the present compounds can be administered either alone or together with other therapeutically active compounds. Such combined treatment can be performed with formulations containing more or all of the therapeutically active compounds, or these may be administered in separate formulations, these being given simultaneously or with suitable intervals.

In the treatment of patients, the daily dose is administered either at one time, or in divided dosages, e.g. two, three, or four times a day.

In the following "Preparations" the methods for preparing new starting materials and intermediates are more specifically described, and these Preparations are followed by Examples which are intended to illustrate but not to limit the invention.

In the preparations and examples described below the following abbreviations are used:

TLC: Thin Layer Chromatography on silica gel 60. Compounds are detected by spraying with 2M sulfuric acid and 10% phosphomolybdic acid in ethanol followed by heating to 150° C.

IR: Infrared absorption spectrum (5% in chloroform).

NMR: Nuclear Magnetic Resonance spectrum measured at 100 MHz in deuterochloroform (CDCl$_3$) with tetramethylsilane (TMS) as internal reference ($\delta$=0.00).

Ether: Diethyl ether.

PREPARATION 1

3-Hexadecyloxy-2-methylenepropan-1-ol

1-Bromohexadecane (61.1 g), diethylformamide (200 ml) and 2-methylenepropane-1,3-diol (17.7 g) were mixed. Sodium hydride dispersion (55-60% in oil, 21.8 g) was added over 10 minutes, and the mixture was then stirred at 55° C. for 1 hour. The reaction mixture was cooled to room temperature and carefully quenched with water (400 ml), extracted with ether (2×200 ml), and the ether extracts were washed with water (200 ml), dried over anhydrous magnesium sulfate, filtered and evaporated to dryness in vacuo. The product was purified through a column of silica gel 60 (70-230 mesh, 30 g) eluting with ether/pentane 1:3. Further purification was achieved by chromatography on Waters PrepLC®/System 500A using a prepPAK®-500/SILICA cartridge with ether/pentane 1:4 followed by ether as eluent.

Mp. 38°-40° C.

Elemental analysis: calculated C 76.86%, H 12.90%, found C 76.82%, H 12.85%.

TLC (ether/pentane 1:1) $R_f$ 0.4.

NMR: $\delta=0.9$ (t, 3H), 1.0-1.8 (m, 28H), 2.21 (t, 1H), 3.42 (t, 2H), 4.03 (s, 2H), 4.16 (d, 2H), 5.12 (m, 2H).

PREPARATION 2

3-Hexadecanoyloxy-2-methylenepropan-1-ol

2-Methylenepropane-1,3-diol (3.0 g) was dissolved in methylene chloride (40 ml). Dicyclohexylcarbodiimide (8.7 g), 4-dimethylaminopyridine (0.4 g) and hexadecanoic acid (8.7 g) were added. The mixture was stirred for 24 hours, filtered, and the filtrate was purified through a column of silica gel 60 (70-230 mesh, 30 g) eluting with ether/chloroform/pentane 1:1:1. The eluate was washed with saturated sodium hydrogen carbonate solution (3×70 ml), dried over anhydrous magnesium sulfate and evaporated to dryness in vacuo. Further purification was achieved by chromatography on a Waters PrepLC®/System 500A using a PrepPAK®-500/SILICA cartridge with ether/chloroform/pentane 1:1:3 as eluent.

NMR: $\delta=0.88$ (t, 3H), 1.0-1.8 (m, 26H), 2.10 (t, 1H), 2.34 (t, 2H), 4.13 (d, 2H), 4.64 (s, 2H), 5.20 (m, 2H).

PREPARATION 3

3-Octadecylaminocarbonyloxy-2-methylenepropan-1-ol

Octadecyl isocyanate (59.1 g) and 2-methylenepropane-1,3-diol (17.7 g) were dissolved and stirred in pyridine (100 ml) for 24 hours at 22° C. Water (200 ml) was added, and the mixture was extracted with chloroform (3×200 ml). The chloroform extracts were washed with water, dried over anhydrous magnesium sulfate, filtered and evaporated to dryness in vacuo. The mixture was purified through a column of silica gel 60 (70-230 mesh, 100 g) eluting with chloroform/ether 1:1. Further purification was achieved by chromatography on a Waters PrepLC®/System 500A using a PrepPAK®-500/SILICA cartridge with chloroform/ether/pentane 1:1:3 as eluent. The product was recrystallized from acetone.

Mp. 71°-73° C.

Elemental analysis: calculated C 71.99%, H 11.82%, N 3.65%, found C 71.93%, H 11.93%, N 3.64%.

TLC (chloroform/ether 1:1) $R_f$ 0.5.

IR (CHCl$_3$): 3450, 2925, 2850, 1710, 1518 cm$^{-1}$.

NMR: $\delta=0.9$ (t, 3H), 1.1-1.7 (m, 32H), 2.4 (t, 1H), 3.17 (m, 2H), 4.12 (d, 2H), 4.64 (s, 2H), 4.75 (m, 1H), 5.17 (m, 2H).

PREPARATION 4

3-Pentadecylaminocarbonyloxy-2-methylenepropan-1-ol

Following the procedure described in Preparation 3, replacing octadecyl isocyanate with pentadecyl isocyanate, the desired product was obtained.

Mp. 60°-62° C.

NMR: $\delta=0.88$ (t, 3H), 1.0-1.7 (m, 26H), 2.63 (t, 1H), 3.16 (m, 2H), 4.11 (d, 2H), 4.63 (s, 2H), 4.8 (m, 1H), 5.16 (m, 2H).

PREPARATION 5

3-Hexadecylaminothiocarbonyloxy-2-methylenepropan-1-ol

Hexadecyl isothiocyanate (9.65 g) and 2-methylenepropane-1,3-diol) (3.0 g) were heated with pyridine (17 ml) and 4-dimethylaminopyridine (0.8 g) to 104° C. for 6.5 hours. The mixture was evaporated to dryness in vacuo and chromatographed on a Waters PrepLC® /System 500A using a PrepPAK®-500/SILICA cartridge with ether/chloroform/hexane 2:2:9 as eluent.

PREPARATION 6

3-Hexadecyloxycarbonyloxy-2-methylenepropan-1-ol

2-Methylenepropane-1,3-diol (5.0 g), hexadecyloxycarbonylchloride (17.4 g) and pyridine (4.4 g) was dissolved in methylene chloride (60 ml). The mixture was stirred for 2.5 hours at 22° C. The mixture was purified through a column of silica gel 60 (70-230 mesh, 30 g), eluting with ether/chloroform 1:1. Further purification was achieved by chromatography on a Waters PrepLC®-System 500A using a PrepPAK®-500-SILICA cartridge with ether/chloroform/pentane 1:1:3 as eluent.

NMR: $\delta=0.88$ (t, 3H), 1.1-1.8 (m, 28H), 1.94 (bt, 1H), 4.14 (m, 4H), 4.68 (bs, 2H), 5.24 (m, 2H).

PREPARATION 7

1-Hexadecyloxy-3-[4-(methanesulfonyloxy)butoxy]-2-methylenepropane

3-Hexadecyloxy-2-methylenepropan-1-ol (from Preparation 1) (5.0 g), sodium hydride dispersion (55-60% in oil, 1.55 g), and 1,4-dimethanesulfonyloxybutane (12.5 g) were mixed in dry dimethylformamide (25 ml) and stirred at 50° C. for 1 hour. The mixture was cooled to room temperature and ether (100 ml) was added. The mixture was carefully quenched with water (100 ml). The aqueous phase was separated and extracted with ether (100 ml). The combined ether extracts were washed with water (100 ml), dried over anhydrous magnesium sulfate, filtered and evaporated to dryness in vacuo. The product was purified by chromatography on silica gel 60 (70-230 mesh, 50 g) eluting with ether/pentane 1:2.

Elemental analysis: calculated C 64.88%, H 10.89%, S 6.95%, found C 64.86%, H 10.82%, S 6.76%.

TLC (ether/pentane 1:1) $R_f$ 0.3.

NMR: $\delta=0.9$ (t, 3H), 1.1-2.0 (m, 32H), 2.99 (s, 3H), 3.35 (m, 4H), 3.95 (bs, 4H), 4.26 (t, 2H), 5.15 (bs, 2H).

PREPARATION 8

1-Hexadecyloxy-3-[5-(methanesulfonyloxy)pentyloxy]-2-methylenepropane

3-Hexadecyloxy-2-methylenepropan-1-ol (from Preparation 1) (4.45 g), sodium hydride dispersion (55–60% in oil, 1.4 g), and 1,5-dimethanesulfonyloxypentane (10.9 g) were mixed in dry dimethylformamide (33 ml) and stirred at 54° C. for 20 hours. Following the work-up procedure described in Preparation 7, the desired product was obtained.

PREPARATION 9

1-Octadecylaminocarbonyloxy-3-(6-bromohexanoyloxy)-2-methylenepropane

3-Octadecylaminocarbonyloxy-2-methylenepropan-1-ol (from Preparation 3) (1.62 g), dicyclohexylcarbodiimide (1.08 g), 4-dimethylaminopyridine (52 mg), and 6-bromohexanoic acid (0.91 g) were stirred in ether (50 ml) for 20 hours at 22° C. Chloroform (50 ml) was added, and the mixture was filtered. The filtrate was purified through a column of silica gel 60 (70–230 mesh, 40 g) eluting with chloroform/ether 1:1. Further purification was achieved by chromatography on a Waters PrepLC®/System 500A using a PrepPAK®-500/SILICA cartridge with chloroform/ether/pentane 1:1:3 as eluent.

TLC (chloroform/ether/pentane 1:1:1) $R_f$ 0.75.

NMR: $\delta = 0.9$ (t, 3H), 1.2–2.0 (m, 38H), 2.37 (t, 2H), 3.17 (m, 2H), 3.40 (t, 2H), 4.60 (s, 4H), 4.7 (m, 1H), 5.24 (bs, 2H).

PREPARATION 10

1-Octadecylaminocarbonyloxy-3-(5-bromopentanoyloxy)-2-methylenepropane

Following the procedure described in Preparation 9, replacing 6-bromohexanoic acid with 5-bromopentanoic acid, the desired product was obtained.

NMR: $\delta = 0.9$ (t, 3H), 1.1–1.65 (m, 32H), 1.7–2.0 (m, 4H), 2.39 (t, 2H), 3.17 (m, 2H), 3.41 (t, 2H), 4.60 (s, 4H), 4.7 (m, 1H), 5.24 (bs, 2H).

PREPARATION 11

1-Octadecylaminocarbonyloxy-3-(8-bromooctanoyloxy)-2-methylenepropane

Following the procedure described in Preparation 9, but replacing 6-bromohexanoic acid with 8-bromooctanoic acid, the desired product was obtained.

NMR: $\delta = 0.88$ (t, 3H), 1.0–2.0 (m, 42H), 2.34 (t, 2H), 3.16 (m, 2H), 3.40 (t, 2H), 4.60 (bs, 4H), 4.65 (m, 1H), 5.24 (bs, 2H).

PREPARATION 12

1-Pentadecylaminocarbonyloxy-3-(6-bromohexanoyl)-2-methylenepropane

Following the procedure described in Preparation 9, but replacing 3-octadecylaminocarbonyloxy-2-methylenepropan-1-ol with 3-pentadecylaminocarbonyloxy-2-methylenepropan-1-ol (from Preparation 4), the desired product was obtained.

NMR: $\delta = 0.88$ (t, 3H), 1.0–2.0 (m, 32H), 2.30 (t, 2H), 3.16 (m, 2H), 3.40 (t, 2H), 4.60 (bs, 4H), 4.65 (m, 1H), 5.25 (bs, 2H).

PREPARATION 13

1-Pentadecylaminocarbonyloxy-3-(8-bromooctanoyloxy)-2-methylenepropane

Following the procedure described in Preparation 9, but replacing 3-octadecylaminocarbonyloxy-2-methylenepropan-1-ol with 3-pentadecylaminocarbonyloxy-2-methylenepropan-1-ol (from Preparation 4), and replacing 6-bromohexanoic acid with 8-bromooctanoic acid, the desired product was obtained.

NMR: $\delta = 0.88$ (t, 3H), 1.0–2.0 (m, 36H), 2.34 (t, 2H), 3.16 (m, 2H), 3.39 (t, 2H), 4.59 (bs, 4H), 4.65 (m, 1H), 5.24 (bs, 2H).

PREPARATION 14

1-Octadecylaminocarbonyloxy-3-(4-bromobutylaminocarbonyloxy)-2-methylenepropane 3-Octadecylaminocarbonyloxy-2-methylenepropan-1-ol (from Preparation 3) (2.0 g) was dissolved in methylene chloride (40 ml). 4-Dimethylaminopyridine (0.13 g) and 4-bromobutyl isocyanate (1.30 g) were added, and the mixture was stirred for 22 hours at 22° C. Ether (40 ml) was added, and the mixture was purified through a column of silica gel 60 (70–230 mesh, 20 g) eluting with ether/chloroform 1:1. Further purification was achieved by chromatography on a Waters PrepLC®/System 500A using a PrepPAK®-500/SILICA cartridge with ether/chloroform/pentane 1:1:2 as eluent.

NMR: $\delta = 0.9$ (t, 3H), 1.1–2.0 (m, 36H), 3.2 (m, 4H), 3.42 (t, 2H), 4.59 (s, 4H), 5.22 (s, 2H).

PREPARATION 15

1-Octadecylaminocarbonyloxy-3-(2-bromoethylaminocarbonyloxy)-2-methylenepropane Following the procedure described in Preparation 14, but replacing 4-bromobutyl isocyanate with 2-bromoethyl isocyanate, the desired product was obtained.

NMR: $\delta = 0.9$ (t, 3H), 1.1–1.6 (m, 32H), 3.16 (m, 2H), 3.3–3.7 (m, 4H), 4.61 (s, 4H), 5.24 (s, 2H).

PREPARATION 16

1-Hexadecyloxy-3-(4-bromobutylaminocarbonyloxy)-2-methylenepropane

3-Hexadecyloxy-2-methylenepropane-1-ol (from Preparation 1) (2.0 g) was dissolved in ether (40 ml). 4-Dimethylaminopyridine (0.16 g) and 4-bromobutyl isocyanate (1.6 g) were added, and the mixture was stirred for 22 hours at 22° C. Chloroform (40 ml) was added, and the mixture was purified through a column of silica gel 60 (70–230 mesh, 20 g) eluting with ether/chloroform 1:1. Further purification was achieved by chromatography on a Waters PrepLC®/System 500A using a prepPAK®-500/SILICA cartridge with ether/chloroform 1:1 as eluent.

NMR: $\delta = 0.88$ (t, 3H), 1.26 (bs, 26H), 1.3–2.0 (m, 6H), 3.21 (q, 2H), 3.35 (t, 2H), 3.39 (t, 2H), 3.97 (bs, 2H), 4.58 (bs, 2H), 4.60 (bs, 1H), 5.18 (bs, 2H).

PREPARATION 17

1-Hexadecyloxy-3-(2-bromoethylaminocarbonyloxy)-2-methylenepropane

Following the procedure described in Preparation 16, but replacing 4-bromobutyl isocyanate with 2-bromoethyl isocyanate, the desired product was obtained.

NMR: δ=0.88 (t, 3H), 1.26 (bs, 26H), 1.50 (m, 2H), 3.42 (q, 2H), 3.50 (m, 4H), 3.97 (bs, 2H), 4.61 (bs, 2H), 5.00 (bs, 1H), 5.19 (bs, 2H).

PREPARATION 18

1-Hexadecyloxy-3-(6-bromohexanoyloxy)-2-methylenepropane

3-Hexadecyloxy-2-methylenepropan-1-ol (from Preparation 1) (1.8 g) was dissolved in ether (35 ml). Dicyclohexylcarbodiimide (1.5 g), 4-dimethylaminopyridine (0.07 g) and 6-bromohexanoic acid (1.2 g) was added, and the mixture was stirred at 22° C. for 18 hours. The reaction mixture was filtered, and the filtrate was washed with water (35 ml), 5% acetic acid in water (35 ml) and water (35 ml). The ether solution was dried over anhydrous magnesium sulfate, filtered and evaporated in vacuo. The crude product was purified by chromatography on a Waters PrepLC ®/System 500A using a PrepPAK ®-500/SILICA cartridge first with ether/pentane 1:4 and in a second run with methylene chloride/hexane 1:4 as eluent.

NMR: δ=0.9 (t, 3H), 1.1–2.0 (m, 34H), 2.36 (t, 2H), 3.40 (t, 4H), 3.97 (bs, 2H), 4.60 (bs, 2H), 5.20 (m, 2H).

PREPARATION 19

1-Hexadecyloxy-3-bromoacetoxy-2-methylenepropane

Following the procedure described in Preparation 18, but replacing 6-bromohexanoic acid with bromoacetic acid, the desired product was obtained.

NMR: δ=0.9 (t, 3H), 1.1–2.0 (m, 28H), 3.40 (t, 2H) 3.85 (s, 2H), 3.98 (bs, 2H), 4.70 (bs, 2H), 5.24 (bs, 2H).

PREPARATION 20

1-Hexadecyloxy-3-(4-bromobutanoyloxy)-2-methylenepropane

Following the procedure described in Preparation 18, but replacing 6-bromohexanoic acid with 4-bromobutanoic acid, the desired product was obtained.

PREPARATION 21

1-Hexadecyloxy-3-(11-bromoundecanoyloxy)-2-methylenepropane

Following the procedure described in Preparation 18, but replacing 6-bromohexanoic acid with 11-bromoundecanoic acid, the desired product was obtained.

NMR: δ=0.9 (t, 3H), 1–2 (m, 44H), 2.34 (t, 2H), 3.40 (t, 4H), 3.97 (bs, 2H), 4.59 (bs, 2H), 5.20 (m, 2H).

PREPARATION 22

1-Hexadecanoyloxy-3-(6-bromohexanoyloxy)-2-methylenepropane

Following the procedure described in Preparation 9, but replacing 3-octadecylaminocarbonyloxy-2-methylenepropan-1-ol with 3-hexadecanoyloxy-2-methylenepropan-1-ol (from Preparation 2), the desired product was obtained.

NMR: δ=0.88 (t, 3H), 1.1–2.0 (m, 32H), 2.3 (m, 4H), 3.40 (t, 2H), 4.60 (bs, 4H), 5.26 (bs, 2H).

PREPARATION 23

1-Hexadecanoyloxy-3-(4-bromobutylaminocarbonyloxy)-2-methylenepropane

Following the procedure described in Preparation 14, but replacing 3-octadecylaminocarbonyloxy-2-methylenepropan-1-ol with 3-hexadecanoyloxy-2-methylenepropan-1-ol (from Preparation 2), the desired product was obtained.

PREPARATION 24

1-Hexadecylaminothiocarbonyloxy-3-(6-bromohexanoyloxy)-2-methylenepropane

Following the procedure described in Preparation 9, but replacing 3-octadecylaminocarbonyloxy-2-methylenepropan-1-ol with 3-hexadecylaminothiocarbonyloxy-2-methylenepropan-1-ol (from Preparation 5), the desired product was obtained.

NMR: δ=0.88 (t, 3H), 1.25 (s, 28H), 1.1–2.0 (m, 6H), 2.38 (t, 2H), 3.1–3.5 (m, 4H), 4.62 (bs, 2H), 4.98 (m, 2H), 5.28 (bs, 2H), 6.2–6.8 (m, 1H).

PREPARATION 25

1-Hexadecyloxycarbonyloxy-3-(6-bromohexanoyloxy)-2-methylenepropane

Following the procedure described in Preparation 9, but replacing 3-octadecylaminocarbonyloxy-2-methylenepropan-1-ol with 3-hexadecyloxycarbonyloxy-2-methylenepropan-1-ol (from Preparation 6), the desired products was obtained.

NMR: δ=0.88 (s, 3H), 1.25 (s, 28H), 1.2–2.0 (m, 6H), 2.33 (t, 2H), 3.40 (t, 2H), 4.13 (t, 2H), 4.63 (bs, 4H), 5.31 (s, 2H).

PREPARATION 26

3-Octadecylaminocarbonyloxy-2-isopropylidenepropan-1-ol

Following the procedure described in Preparation 3, but replacing 2-methylenepropane-1,3-diol with 2-isopropylidenepropane-1,3-diol, the desired product was obtained.

NMR: δ=0.88 (t, 3H), 1.26 (bs, 32 H), 1.81 (bs, 1H), 2.60 (bs, 1H), 3.14 (q, 2H), 4.17 (s, 2H), 4.70 (s, 3H).

PREPARATION 27

1-Octadceylaminocarbonyloxy-3-(6-bromohexanoyloxy)-2-isopropylidenepropane

Following the procedure described in Preparation 9, but replacing 3-octadecylaminocarbonyloxy-2-methylenepropan-1-ol with 3-octadecylaminocarbonyloxy-2-isopropylidenepropan-1-ol (from Preparation 26), the desired compound was obtained.

NMR: δ=0.86 (t, 3H), 1.26 (s, 32H), 1.1–1.9 (m, 6H), 1.82 (s, 3H), 1.84 (s, 3H), 2.32 (t, 2H), 3.14 (q, 2H), 3.40 (t, 2H), 4.6 (bs, 1H), 4.68 (bs, 4H).

PREPARATION 28

3-Octadecylaminocarbonyloxy-2-ethylidenepropan-1-ol

Following the procedure described in Preparation 3, but replacing 2-metyylenepropane-1,3-diol with 2-ethylidenepropane-1,3-diol an approx. 1:1 mixture of E- and Z-isomers of the desired compound is obtained.

PREPARATION 29

1-Octadecylaminocarbonyloxy-3-(6-bromohexanoyloxy)-2-ethylidenepropane

Following the procedure described in Preparation 9, but replacing 3-octadecylaminocarbonyloxy-2-methylenepropan-1-ol with an approx. 1:1 mixture of E- and Z-isomers of 3-octadceylaminocarbonyloxy-2-ethylidenepropan-1-ol (from Preparation 28), an approx 1:1 mixture of E- and Z-isomers of the desired compound is obtained.

PREPARATION 30

1-Hexadecanoyloxy-3-(8-bromooctanoyloxy)-2-methylenepropane

Following the procedure described in Preparation 9, but replacing 3-octadecylaminocarbonyloxy-2-methylenepropan-1-ol with 3-hexadecanoyloxy-2-methylenepropan-1-ol (from Preparation 2), and replacing 6-bromohexanoic acid with 8-bromooctanoic acid, the desired product was obtained.

NMR: δ=0.88 (s, 3H), 1.26 (s, 28H9, 1.2–1.9 (m, 8H), 2.34 (t, 4H), 3.39 (t, 2H), 4.59 (s, 4H), 5.25 (s, 2H).

PREPARATION 31

1-Octadecylaminocarbonyloxy-3-(7-bromoheptanoyloxy)-2-methylenepropane

Following the procedure described in Preparation 9, but replacing 6-bromohexanoic acid with 7-bromoheptanoic acid, the desired product was obtained.

M.p. 49° C. (from methanol).

Elemental analysis: calculated C 62.70%, H9.82%, N 2.445, found C 62.83%, H 9,79%, N 2.56%.

NMR: δ=0.87 (t, 3H), 1,26 (s, 34H), 1.1–2.0 (m, 6H), 2.35 (t, 2H), 3.14 (q, 2H), 3.40 (t, 2H), 4.60 (s, 4H), 4.65 (m, 1H), 5.24 (m, 2H).

PREPARATION 32

1-Octadecylaminocarbonyloxy-3-[7-(methanesulfonyloxy)heptanoxyloxy]-2-methylenepropane Following the procedure described in Preparation 9, but replacing 6-bromohexanoic acid with 7-(methanesulfonyloxy)heptanoic acid, the desired product was obtained.

NMR: δ=0.88 (t, 3H), 1.25 (s, 32H), 1.0–1.8 (m, 8H), 2.32 (t, 2H), 2.99 (s, 3H), 3.16 (q, 2H), 4.22 (t, 2H), 4.59 (s, 4H), 4.70 (m, 1H), 5.23 (bs, 2H).

PREPARATION 33

1-Octadecylaminocarbonyloxy-3-[8-(1-imidazolyl)octanoyloxy]-2-methylenepropane 1-Octadecylaminocarbonyloxy-3-(8-bromooctanoyloxy)-2-methylenepropane (from Preparation 11) (1.18 g) and imidazole (0.68 g) were stirred in toluene (20 ml) at 104° C. for 14 hours. The mixture was cooled and evaporated in vacuo. The residue was chromatographed on silica gel 60 (70–230 mesh, 40 g) with ether/chloroform/triethylamine (1:1:0.04) as eluent to give the desired product.

NMR: δ=0.87 (t, 3H), 1.25 (s, 36H), 1.2–1.8 (m, 6H), 2.33 (t, 2H), 3.16 (q, 2H), 3.91 (t, 2H), 4.59 (4.95 (bt, 1H), 5.22 (s, 2H), 6.89 (s, 1H), 7.04 (s, 1H), 7.40 (s, 1H).

PREPARATION 34

1-Octadecylaminocarbonyloxy-3-[6-(1-imidazolyl)hexanoyloxy]-2-methylenepropane Following the procedure described in Preparation 33, but replacing 1-octadecylaminocarbonyloxy-3-(8-bromooctanoyloxy)-2-methylenepropane with 1-octadecylaminocarbonyloxy-3-(6-bromohexanoyloxy)-2-methylenepropane (from Preparation 9), the desired product was obtained.

NMR: δ=0.88 (t, 3H), 1.25 (s, 32H), 1.0–2.0 (m, 6H), 2.34 (t, 2H), 4.16 (q, 2H), 3.93 (t, 2H), 4.58 (s, 4H), 5.06 (m, 1H), 5.23 (s, 2H), 6.89 (s, 1H), 7.03 (s, 1H), 7.45 (s, 1H).

PREPARATION 35

1-Octadeyclaminocarbonyloxy-3-(5-bromopentylaminocarbonyloxy)-2-methylenepropane Following the procedure described in Preparation 14, but replacing 4-bromobutyl isocyanate with 5-bromopentyl isocyanate, the desired products was obtained.

NMR: δ=0.87 (t, 3H), 1.25 (s, 32H), 1.0–2.0 (m, 6H), 3.15 (m, 4H), 3.40 (t, 2H), 4.59 (s, 4H), 4.65 (m, 2H), 5.22 (s, 2H).

PREPARATION 36

1-Octadecylaminocarbonyloxy-3-(7-bromoheptylaminocarbonyloxy)-2-methylenepropane Following the procedure described in Preparation 14, but replacing 4-bromobutyl isocyanate with 7-bromoheptyl isocyanate, the desired product was obtained.

NMR: δ=0.88 (t, 3H, 1.26 (s, 32H), 1.0–2.0 (m, 10H), 3.16 (q, 4H), 3.40 (t, 2H), 4.59 (s, 3h), 4.70 (bs, 2H), 5.22 (s, 2H).

PREPARATION 37

3-Octadecyloxycarbonyloxy-2-methylenepropan-1-ol

Following the procedure described in Preparation 6, but replacing hexadecyloxycarbonyl chloride with octadecyloxycarbonyl chloride, the desired product was obtained.

NMR: δ=0.88 (t, 3H), 1.26 (s, 32H), 2.0 (ts, 1H), 4.13 (t, 2H), 4.16 (s, 2H), 4.68 (s, 2H), 5.23 (m, 2H).

PREPARATION 38

1-Octadecyloxycarbonyloxy-3-(7-bromoheptanoyloxy)-2-methylenepropane

Following the procedure described in Preparation 9, but replacing 3-octadecylaminocarbonyloxy-2-methylenepropan-1-ol with 3-octadecyloxycarbonyloxy-2-methylenepropan-1-ol and 6-bromohexanoic acid with 7-bromoheptanoic acid, the desired product was obtained.

NMR: δ=0.88 (t, 3H), 1.26 (s, 32H), 1.2–2.0 (m, 8H), 2.35 (t, 2H), 3.40 (t, 2H), 4.13 (t, 2H), 4.63 (s, 4H), 5.31 (s, 2H).

PREPARATION 39

1-Hexadecyloxycarbonyloxy-3-(8-bromooctanoyloxy)-2-methylenepropane

Following the procedure described in Preparation 9, but replacing 3-octadecylaminocarbonyloxy-2-methylenepropan-1-ol with 3-hexadceyloxycarbonyloxy-2-methylenepropan-1-ol and 6-bromohexanoic acid with 8-bromooctanoic acid, the desired product was obtained.

NMR: δ=0.88 (s, 3H), 1.25 (bs, 28H), 1.2–1.9 (m, 10H), 2.30 (t, 2H), 3.40 (t, 2H), 4.13 (t, 2H), 4.64 (bs, 4H), 5.31 (m, 2H).

PREPARATION 40

1-octadecylaminocarbonyloxy-3-(8-bromooctanoyloxy)-2-isopropylidenepropane

Following the procedure described in Preparation 9, but replacing 3-octadecylaminocarbonyloxy-2-methylenepropan-1-ol with 3-octadecylaminocarbonyloxy-2-isopropylidenepropan-1-ol (from Preparation 26) and 6-bromohexanoic acid with 8-bromooctanoic acid, the desired product was obtained.

NMR: δ=0.88 (s, 3H), 1.25 (bs, 30H), 1.1–1.8 (m, 12H), 1.83 (s, 3H), 1.85 (s, 3H), 2.30 (t, 2H), 3.14 (q, 2H), 3.39 (t, 2H), 4.55 (bs, 1H), 4.67 (bs, 4H).

PREPARATION 41

3-Pentadecylaminocarbonyl-2-isopropylidenepropan-1-ol

Following the procedure described in Preparation 3, but replacing octadecyl isocyanate with pentadecyl isocyanate and 2-methylenepropane-1,3-diol with 2-isopropylidenepropan-1,3-diol, the desired product was obtained.

NMR: δ=0.88 (t, 3H), 1.25 (bs, 26H), 1.81 (s, 6H), 2.65 (bs, 1H), 3.15 (q, 2H), 4.17 (s, 2H), 4.70 (bs, 3H).

PREPARATION 42

1-Pentaceylaminocarbonyloxy-3-(8-bromooctanoyloxy)-2-isopropylidenepropane

Following the procedure described in Preparation 9, but replacing 3-octadeyclaminocarbonyloxy-2-methylenepropan-1-ol with 3-pentadecylaminocarbonyloxy-2-isopropylidenepropan-1-ol (from Preparation 41) and 6-bromohexanoic acid with 8-bromooctanoic acid, the desired products was obtained.

NMR: δ=0.88 (t, 3H), 1.25 (bs, 26H), 1.1–1.8 (m, 10H), 1.82 (s, 3H), 1.84 (s, 3H), 2.30 (t, 2H), 3.10 (q, 2H), 3.39 (t, 2H), 4.60 (bs, 1H), 4.66 (bs, 4H).

PREPARATION 43

1-Pentadecylaminocarbonyloxy-3-(6-bromohexanoyloxy)-2-isopropylidenepropane

Following the procedure described in Preparation 9, but replacing 3-octadecylaminocarbonyloxy-2-methylenepropan-1-ol with 3-pentadecylaminocarbonyloxy-2-isopropylidenepropan-1-ol (from Preparation 41), the desired product was obtained.

NMR: δ=0.88 (t, 3H), 1.25 (bs, 26H), 1.1–1.9 (m, 6H), 1.82 (s, 3H), 1.84 (s, 3H), 2.32 (t, 2H), 3.14 (q, 2H), 3.40 (t, 2H), 4.67 (bs, 5H).

PREPARATION 44

3-(6-Bromohexanoyloxy)-2-methylenepropan-1-ol

2-Methyllenepropane-1,3-diol (5.0 g), 6-bromohexaoic acid (11.1 g), 4-dimethylaminopyridine 0.7 g) and dicyclohexylcarbodiimide (14.5 g) were mixed in methylene chloride (60 ml). After stirring for 4 hours at 22° C. ether was added, the mixture was filtered, and the filtrate was purified through a column of silica gel 60 (70–230 mesh, 30 g), eluting with ether/chloroform 1:1. Further purification was achieved by chromatography on Waters PrepIC®/System 500A using a prep-PAK®-500 /SILICA cartridge with ether/chloroform/pentane 1:1:3 as eluent.

NMR: δ=1.3–2.0 (m, 6H), 2.33 (m, 3H), 3.41 (t, 2H), 4.13 (d, 2H), 4.65 (s, 2H), 5.20 (m, 2H).

PREPARATION 45

1-Tridecylaminocarbonyloxy-3-(6-bromohexanoyloxy)-2-methylenepropane 3-(6-Bromohexanoyloxy)-2-methylenepropan-1-ol (from Preparation 44) (0.58 g), tridecyl isocyanate (0.55 g) and 4-dimethylaminopyridine (0.05 g) were mixed in methylene chloride (3 ml). After stirring for 23 hours at 22° C. the mixture was filtered, and the filtrate was purified through a column of silica gel 60 (70–230 mesh, 4 g) eluting with ether/chloroform 1:1. Further purification was achieved by chromatography on Waters PrepLC®/System 500A using a prepPAK®-500/SILICA cartridge with ether/chloroform/pentane 1:1:4 as eluent.

NMR: δ=0.88 (s, 3H), 1.25 (s, 22H), 1.1–2.0 (m, 6H), 2.37 (t, 2H), 3.16 (q, 2H), 3.40 (t, 2H), 4.60 (s, 4H), 4.70 (bs, 1H), 5.25 (bs, 2H).

PREPARATION 46

3-[6-(Triphenylmethoxy)hexyloxy]-2-methylenepropan-1-ol

Sodium hydride (from 55–60% oil dispersion (0.52 g) washed with pentane (3×3 ml)), dry dimethylformamide (20 ml), and 2-metyylenepropane-1,3-diol (1.0 g) were mixed. After 1 hour when H₂-evolution had ceased 1-chloro-6-(triphenylmethoxy)hexane (4.2 g) was added, and the mixture was stirred for 3 hours at 85° C. After cooling water (20 ml) was carefully added, and the mixture was extracted with ether (2×100 ml). The ether extracts were washed with water (100 ml), dried over magnesium sulfate and evaporated to dryness in vacuo. The product was purified through a column of silica gel 60 (70–230 mesh, 40 g) eluting with ether. Futher purification was achieved by chromatography on Waters PrepLC®/System 500A using a prepPAK®-500/SILICA cartridge with ether/pentane 1:2 followed by ether/pentane 1:1 as eluent.

NMR: δ=1.1–1.8 (m, 8H), 2.10 (bs, 1H), 3.05 (t, 2H), 3.39 (t, 2H), 4.00 (s, 2H), 4.12 (s, 2H), 5.10 (bd, 2H), 7.0–7.5 (m, 15H).

PREPARATION 47

3-Pentaceylaminocarbonyloxy-1-[6-(triphenylmethoxy)hexyloxy]-2-methylenepropane

A mixture of 3-[6-(triphenylmethoxy)hexyloxy]-2-methylenepropan-1-ol (from Preparation 46) (1.2 g), pentadecyl isocyanate (0.78 g) and 4-dimethylaminopyridine (0.07 g) in methylene chloride (5 ml) was stirred for 5 hours at 22° C. The mixture was evaporated to dryness in vacuo, and the residue was extracted with ether (2×20 ml). The ether extracts were evaporated to dryness in vacuo, and the product was purified through a column of silica gel 60 (70–230 mesh, 15 g) eluting with ether/methylene chloride 1:1. Further purification was achieved by chromatography on Waters PrepLC®/System 500A using a prepPAK®-500/SILICA cartridge with ether/methylene chloride/pentane 1:1:3 as eluent.

NMR: δ=0.88 (t, 3H), 1.25 (s, 26H), 1.2–1.8 (m, 8H), 3.15 (m, 4H), 3.38 (t, 2H), 3.95 (s, 2H), 4.57 (s, 2H), 4.70 (m, 1H), 5.16 (s, 2H), 7.2–7.5 (m, 15H).

PREPARATION 48

3-Octadecylaminocarbonyloxy-1-[6-(triphenylmethoxy)hexyloxy]-2-methylenepropane

Following the procedure described in Preparation 47, but replacing pentadecyl isocyanate with octadecyl isocyanate, the desired product was obtained.

NMR: δ=0.88 (t, 3H), 1.26 (s, 32H), 1.1–1.7 (m, 8H), 3.10 (m, 4H), 3.38 (t, 2H), 3.95 (s, 2H), 4.57 (s, 2H), 4.60 (m, 1H), 5.17 (s, 2H), 7.1–7.4 (m, 15H).

PREPARATION 49

3-Octadecyloxycarbonyloxy-1-[6-(triphenylmethoxy)-hexyloxyl]-2-methylenepropane

A mixture of 3-[6-(triphenylmethoxy)hexyloxy]-2-metylenepropane-1-ol (from Preparation 46) (1.5 g) and pyridine (4.5 ml) in methylene chloride (15 ml) was cooled in an ice/water bath and octadecyloxycarbonyl chloride (1.3 g) was added. After stirring for 10 minutes at 0° C. the temperature was raised to 22° C. for 5 hours. Ether (15 ml) was added, and the mixture was filtered. The filtrate was evaporated to dryness in vacuo, and the residue was purified through a column of silica gel 60 (70–230 mesh, 15 g) eluting with ether/methylene chloride 1:1. Further purification was achieved by chromatography on Waters PrepLC®/System 500A using a prepPAK®-500/SILICA cartridge with ether/methylene chloride/pentane 1:1:3 as eluent.

NMR: $\delta = 0.88$ (t, 3H), 1.26 (s, 32H), 1.0–1.8 (m, 8H), 3.05 (t, 2H), 3.38 (t, 2H), 3.97 (s, 2H), 4.12 (t, 2H), 4.63 (s, 2H), 5.25 (s, 2H), 7.1–7.5 (m, 15H).

PREPARATION 50

3-Hexadecyloxycarbonyloxy-1-[6-(triphenylmethoxy)-hexyloxy]-2-methylenepropane

Following the procedure described in Preparation 49, but replacing octadecyloxycarbonyl chloride with hexadecyloxycarbonyl chloride, the desired product was obtained.

NMR: $\delta = 0.88$ (t, 3H), 1.2–1.8 (m, 8H), 1.26 (s, 28H), 3.05 (t, 2H), 3.38 (t, 2H), 3.97 (s, 2H), 4.12 (t, 2H), 4.63 (s, 2H), 5.25 (s, 2H), 7.1–7.5 (m, 15H).

PREPARATION 51

3-Hexadecyloxycarbonyloxy-1-(6-hydroxyhexyloxy)-2-methylenepropane

3-Hexadecyloxycarbonyloxy-1-[6-(triphenylmethoxy)hexyloxy]-2-methylenepropane (from Preparation 50) (1.95 g), 4-toluenesulfonic acid monohydrate (60 mg) and water (0.15 ml) were stirred in methylene chloride (30 ml) for 24 hours at 22° C. The reaction mixture was neutralized with saturated aqueous sodium hydrogencarbonate, dried over magnesium sulfate, filtered and evaporated in vacuo to dryness. Purification was achieved by chromatography on Waters PrepLC® /System 500A using a prepPAK®-500 cartridge with ether/chloroform/pentane 1:1:10 followed by ether/chloroform 1:1 as eluents.

NMR: $\delta = 0.88$ (t, 3H), 1.16 (s, 30H), 1.2–1.8 (m, 7H), 3.41 (t, 2H), 3.63 (t, 2H), 3.98 (s, 2H), 4.13 (t, 2H), 4.64 (s, 2H), 5.23 (s, 2H).

PREPARATION 52

3-Octadecyloxycarbonyloxy-1-(6-hydroxyhexyloxy)-2-methylenepropane

Following the procedure described in Preparation 51, but replacing 3-hexadcyloxycarbonyloxy-1-[6-(triphenylmethoxy)hexyloxy]-2-methylenepropane with 3-octadecyloxycarbonyloxy-1-[6-(triphenylmethoxy)-hexyloxy]-2-methylenepropane (from Preparation 49), the desired product was obtained.

NMR: $\delta = 0.87$ (t, 3H), 1.25 (s, 32H), 1.2–1.8 (m, 9H), 3.41 (t, 2H), 3.63 (t, 2H), 4.07 (s, 2H), 4.13 (t, 2h), 4.64 (s, 2H), 5.23 (s, 2H).

PREPARATION 53

3-Octadecylaminocarbonyloxy-1-(6-hydroxyhexyloxy)-2-methylenepropane

Following the procedure described in Preparation 51, but replacing 3-hexadecyloxycarbonyloxy-1-[6-(triphenylmethoxy)hexyloxy]-2-methylenepropane with 3-octadecylaminocarbonyloxy-1-[6-(triphenylmethoxy)hexyloxy]-2-methylenepropane (from Preparation 48), the desired product was obtained.

NMR: $\delta = 0.87$ (t, 3H), 1.25 (s, 32H), 1.0–1.8 (m, 8H), 3.14 (m, 3H), 3.40 (t, 2H), 3.62 (t, 2H), 3.95 (s, 2H), 4.56 (s, 2H), 4.60 (bs, 1H), 5.16 (s, 2H).

PREPARATION 54

3-Pentadecylaminocarbonyloxy-1-(6-hydroxyhexyloxy)-2-methylenepropane

Following the procedure described in Preparation 51, but replacing 3-hexadecyloxycarbonyloxy-1-[6-(triphenylmethoxy)hexyloxy]-2-methylenepropane with 3-pentadecylaminocarbonyloxy-1-[6-(triphenylmethoxy)hexyloxy]-2-methylenepropane, the desired product was obtained.

NMR: $\delta = 0.87$ (t, 3H), 1.25 (s, 26H), 1.2–1.7 (m, 8H), 1.86 (s, 1H), 3.14 (q, 2H), 3.41 (t, 2H), 3.62 (t, 2H), 3.96 (s, 2H), 4.58 (s, 2H), 4.70 (m, 1H), 5.17 (s, 2H).

PREPARATION 55

3-Hexadecyloxycarbonyloxy-1-[6-(methanesulfonyloxy)hexyloxy]-2-methylenepropane

3-Hexadecyloxycarbonyloxy-1-(6-hydroxyhexyloxy)-2-methylenepropane (from Preparation 51) (0.54 g) and methanesulfonyl chloride (0.20 g) were stirred in methylene chloride at 0° C. Pyridine (6 ml) was added and stirring continued for 15 minutes at 0° C. and for 2.5 hours at 22° C. Methylene chloride (10 ml) was added, and the organic phase was washed with water (3×15 ml), dried over magnesium sulfate, filtered and evaporated in vacuo to dryness. Purification was achieved by chromatography on silica gel 60 (70–230 mesh, 15 g) eluting with chloroform/ether/pentane 1:1:10 followed by chloroform/ether 1:1.

NMR: $\delta = 0.87$ (t, 3H), 1.25 (s, 28H), 1.0–1.8 (m, 8H), 2.99 (s, 3H), 3.41 (t, 2H), 3.98 (s, 2H), 4.12 (t, 2H), 4.22 (t, 2H), 4.64 (s, 2H), 5.23 (s, 2H).

PREPARATION 56

3-Octadecyloxycarbonyloxy-1-[6-(methanesulfonyloxy)hexyloxy]-2-methylenepropane

Following the procedure described in Preparation 55, but replacing 3-hexadecyloxycarbonyloxy-1-(6-hydroxyhexyloxy)-2-methylenepropane with 3-octadecyloxycarbonyloxy-1-(6-hydroxyhexyloxy)-2-methylenepropane (from Preparation 52), the desired product was obtained.

NMR: $\delta = 0.88$ (t, 3H), 1.26 (s, 32H), 1.0–2.0 (m, 8H), 3.00 (s, 3H), 3.41 (t, 2H), 3.98 (s, 2H), 4.13 (t, 2H), 4.22 (t, 2H), 4.64 (s, 2H), 5.23 (s, 2H).

PREPARATION 57

3-pentadecylaminocarbonyloxy-1-[6-(methanesulfonyloxy)hexyloxy]-2-methylenepropane Following the procedure described in Preparation 55, but replacing 3-hexadecyloxycarbonyloxy-1-(6-hydroxyhexyloxy)-2-methylenepropane with 3-pentadecylaminocarbonyloxy-1-(6-hydroxyhexyloxy)-2- methylenepropane (from Preparation 54), the desired product was obtained.

NMR: δ=0.88 (t, 3H), 1.26 (s, 26H), 1.1–1.9 (m, 8H), 3.00 (s, 3H), 3.16 (q, 2H), 3.41 (t, 2H), 3.96 (s, 2H), 4.22 (t, 2H), 4.58 (s, 2H), 4.70 (m, 1H), 5.18 (s, 2H).

PREPARATION 58

3-Octadecylaminocarbonyloxy-1-[6-(methanesulfonyloxy)hexyloxy]-2-methylenepropane Following the procedure described in Preparation 55, but replacing 3-hexadecyloxycarbonyloxy-1-(6-hydroxyhexyloxy)-2-methylenepropane with 3-octadecylaminocarbonyloxy-1-(6-hydroxyhexyloxy)-2-methylenepropane (from Preparation 53), the desired product was obtained.

NMR: δ=0.87 (t, 3H), 1.26 (s, 32H), 1.0–1.8 (m, 8H), 2.99 (s, 3H), 3.12 (q, 2H), 3.40 (t, 2H), 3.96 (s, 2H), 4.22 (t, 2H), 4.57 (s, 2H), 4.70 (bs, 1H), 5.18 (bs, 2H).

EXAMPLE 1

1-Hexadecyloxy-3-[4-(trimethylammonio)butoxy]-2-methylenepropane methanesulfonate 1-Hexadecyloxy-3-[4-(methanesulfonyloxy)butoxy]-2-methylenepropane (from Preparation 7) (1.77 g) was refluxed with 33% trimethylamine in ethanol at 50° C. for 4 hours. Excess trimethylamine and ethanol were removed in vacuo. The product was recrystallized from chloroform/acetone.

Mp. 125°–131° C.

Elemental analysis: calculated C 64.44%, H 11.40%, N 2.68%, S 6.15%, found C 64.39%, H 11.37%, N 2.72%, S 6.05%.

NMR: δ=0.9 (t, 3H), 1–2 (m, 32H), 2.71 (s, 3H), 3.32 (s, 9H), 3.2–3.7 (m, 6H), 3.94 (bs, 4H), 5.14 (bs, 2H).

EXAMPLE 2

1-Hexadecyloxy-3-[4-(3-thiazolio)butoxy]-2-methylenepropane methanesulfonate

1-Hexadecyloxy-3-[4-(methanesulfonyloxy)butoxy]-2-methylenepropane (from Preparation 7) (2.5 g) was heated with thiazole (2 ml) at 60° C. for 4 days. Excess thiazole was removed in vacuo.

NMR: δ=0.9 (t, 3H), 1–1.8 (m, 30H), 1.9–2.3 (m, 2H), 2.76 (s, 3H), 3.2–3.5 (m, 4H), 3.94 (bs, 4H), 4.76 (t, 2H), 5.14 (bs, 2H), 8.4 (m, 2H), 10.7 (bs, 1H).

EXAMPLE 3

1-Hexadecyloxy-3-(4-[5-(2-hydroxyethyl)-4-methyl-3-thiazolio]butoxy)-2-methylenepropane methanesulfonate 1-Hexadecyloxy-3-[4-(methanesulfonyloxy)butoxy]-2-methylenepropane (from Preparation 7) (0.30 g) was heated with 5-(2-hydroxyethyl)-4-methylthiazole at 56° C. for 5 days. Excess 5-(2-hydroxyethyl)-4-methylthiazole was removed in vacuo.

NMR: δ=0.9 (t, 3H), 1–2.2 (m, 32H), 2.50 (s, 3H), 2.69 (s, 3H), 3.05 (t, 2H), 3.2–3.5 (m, 4H), 3.85 (m, 2H), 3.94 (s, 4H), 4.5 (t, 2H), 5.14 (bs, 2H), 10.29 (s, 1H).

EXAMPLE 4

1-Hexadecyloxy-3-[4-(1-pyridinio)butoxy]-2-methylenepropane methanesulfonate

1-Hexadecyloxy-3-[4-(methanesulfonyloxy)butoxy]-2-methylenepropane (from Preparation 7) (1.6 g) was heated with dry pyridine (50 ml) at 50° C. for 28 hours. Excess pyridine was removed in vacuo. The product was recrystallized from chloroform/acetone.

NMR: δ=0.9 (t, 3H), 1.1–1.8 (m, 30H), 1.95–2.5 (m, 2H), 2.75 (s, 3H), 3.25–3.55 (m, 4H), 3.93 (bs, 4H), 4.89 (t, 2H), 5.14 (bs, 2H), 8.1 (t, 2H), 8.5 (t, 1H), 9.3 (d, 2H).

EXAMPLE 5

1-Hexadecyloxy-3-[5-(1-pyridinio)pentyloxy]-2-methylenepropane methanesulfonate

Following the procedure described in Example 4, but replacing 1-hexadecyloxy-3-[4-(methanesulfonyloxy)butoxy]-2-methylenepropane with 1-hexadecyloxy-3-[5-(methanesulfonyloxy)pentyloxy]-2-methylenepropane (from Preparation 8), the desired product was obtained.

NMR: δ=0.9 (t, 3H), 1–1.8 (m, 32H), 1.85–2.3 (m, 2H), 2.75 (s, 3H), 3.39 (m, 4H), 3.92 (bs, 4H), 4.83 (t, 2H), 5.13 (m, 2H), 8.10 (t, 2H), 8.5 (t, 1H), 9.3 (d, 2H).

EXAMPLE 6

1-Octadecylaminocarbonyloxy-3-[6-(1-pyridinio)hexanoyloxy]-2-methylenepropane bromide 1-Octadecylaminocarbonyloxy-3-(6-bromohexanoyloxy)-2-methylenepropane (from Preparation 9) (0.84 g) was dissolved in dry pyridine (20 ml) and heated to 60° C. for 22 hours. Excess pyridine was removed in vacuo.

NMR: δ=0.9 (t, 3H), 1.1–1.9 (m, 36H), 1.9–2.25 (m, 2H), 2.36 (t, 2H), 3.16 (m, 2H), 4.57 (s, 4H), 5.03 (t, 3H), 5.23 (m, 2H), 8.17 (t, 2H), 8.57 (t, 1H), 9.61 (d, 2H).

EXAMPLE 7

1-Octadecylaminocarbonyloxy-3-[5-(1-pyridinio)pentanyloxy]-2-methylenepropane bromide Following the procedure described in Example 6, but replacing 1-octadecylaminocarbonyloxy-3-(6-bromohexanoyloxy)-2-methylenepropane with 1-octadecylaminocarbonyloxy-3-(5-bromopentanoyloxy)-2-methylenepropane (from Preparation 10), the desired product was obtained.

NMR: δ=0.9 (t, 3H), 1.1–2.2 (m, 36H), 2.46 (t, 2H), 3.15 (m, 2H), 4.57 (bs, 4H), 5.1 (m, 2H), 5.23 (m, 2H), 8.1 (t, 2H), 8.5 (t, 1H), 9.6 (d, 2H).

EXAMPLE 8

1-Octadecylaminocarbonyloxy-3-[8-(1-pyridinio)octanoyloxy]-2-methylenepropane bromide Following the procedure described in Example 6, but replacing 1-octadecylaminocarbonyloxy-3-(6-bromohexanoyloxy)-2-methylenepropane with 1-octadecylaminocarbonyloxy)-3-(8-bromooctanoyloxy)-2-methylenepropane (from Preparation 11), the desired product was obtained.

NMR: δ=0.88 (t, 3H), 1.1–1.8 (m, 40H), 1.8–2.2 (m, 2H), 2.32 (t, 2H), 3.15 (m, 2H), 4.58 (bs,4H), 4.9 (m, 1H), 5.03 (t, 2H), 5.24 (bs, 2H), 8.15 (t, 2H), 8.54 (t, 1H), 9.55 (d, 2H).

EXAMPLE 9

1-Octadecylaminocarbonyloxy-3-[6-(3-thiazolio)hexanoyloxy]-2-methylenepropane bromide 1-Octadecylaminocarbonyloxy-3-(6-bromohexanoyloxy)-2-methylenepropane (from Preparation 9) (0.55 g) and thiazole (2.5 ml) were heated to 110° C. for 4 hours. The reaction mixture was evaporated to dryness in vacuo.

NMR: δ=0.88 (t, 3H), 1.0–1.8 (m, 36H), 1.8–2.2 (m, 2H), 2.37 (t, 2H), 3.15 (m, 2H), 4.58 (bs, 4H), 4.88 (t, 2H), 5.0 (m, 1H), 5.23 (bs, 2H), 8.37 (bs, 1H), 8.63 (bs, 1H), 11.15 (bs, 1H).

EXAMPLE 10

1-Octadecylaminocarbonyloxy-3-[5-(3-thiazolio)pentanoyloxy]-2-methylenepropane bromide Following the procedure described in Example 9, but replacing 1-octadecylaminocarbonyloxy-3-(6-bromohexanoyloxy)-2-methylenepropane with 1-octadecylaminocarbonyloxy-3-(5-bromopentanoyloxy)-2-methylenepropane, the desired product was obtained.

NMR: δ=0.88 (t, 3H), 1.0–1.9 (m, 34H), 1.9–2.3 (m, 2H), 2.46 (t, 2H), 3.15 (m, 2H), 4.58 (bs, 4H), 4.7–5.1 (m, 3H), 5.24 (bs, 2H), 8.35 (m, 1H), 8.66 (m, 1H), 11.15 (bs, 1H).

EXAMPLE 11

1-Octadecylaminocarbonyloxy-3-[8-(3-thiazolio)octanoyloxy]-2-methylenepropane bromide Following the procedure described in Example 9, but replacing 1-octadecylaminocarbonyloxy-3-(6-bromohexanoyloxy)-2-methylenepropane with 1-octadecylaminocarbonyloxy-3-(8-bromooctanoyloxy)-2-methylenepropane (from Preparation 11), the desired product was obtained.

NMR: δ=0.88 (t, 3H), 1–1.75 (m, 40H), 1.75–2.2 (m, 2H), 2.33 (t, 2H), 3.15 (m, 2H), 4.58 (bs, 4H), 4.87 (t, 2H), 4.9 (m, 1H), 5.24 (bs, 2H), 8.41 (bs, 1H), 8.61 (bs, 1H), 11.18 (bs, 1H).

EXAMPLE 12

1-Pentadecylaminocarbonyloxy-3-[6-(3-thiazolio)hexanoyloxy]-2-methylenepropane bromide Following the procedure described in Example 9, but replacing 1-octadecylaminocarbonyloxy-3-(6-bromohexanoyloxy)-2-methylenepropane with 1-pentadecylaminocarbonyloxy-3-(6-bromohexanoyloxy)-2-methylenepropane (from Preparation 12), the desired product was obtained.

NMR: δ=0.88 (t, 3H), 1.1–2.0 (m, 30H), 2.1 (m, 2H), 2.37 (t, 2H), 3.15 (q, 2H), 4.58 (bs, 4H), 4.85 (t, 2H), 4.9 (m, 1H), 5.28 (bs, 2H), 8.36 (m, 1H), 8.63 (d, 1H), 10,84 (bs, 1H).

EXAMPLE 13

1-Pentadecylaminocarbonyloxy-:3-[8-(3-thiazolio)octanoyloxy]-2-methylenepropane bromide Following the procedure described in Example 9, but replacing 1-octadecylaminocarbonyloxy-3-(6-bromohexanoyloxy)-2-methylenepropane with 1-pentanoylaminocarbonyloxy-3-(8-bromooctanoyloxy)-2-methylenepropane (from Preparation 13), the desired product was obtained.

NMR: δ=0.88 (t, 3H), 1.1–2.2 (m, 36H), 2.33 (t, 2H), 3.15 (q, 2H), 4.58 (bs, 4H), 4.86 (t, 2H), 4.8 (m, 1H), 5.24 (bs, 2H), 8.37 (m, 1H), 8.53 (d, 1H), 10.83 (bs, 1H).

EXAMPLE 14

1-Octadecylaminocarbonyloxy-3-[6-(trimethylammonio)hexanoyloxy]-2-methylenepropane bromide 1-Octadecylaminocarbonyloxy-3-(6-bromohexanoyloxy)-2-methylenepropane (from Preparation 9) (0.84 g) was dissolved in 33% trimethylamine in ethanol (30 ml) and heated to 60° C. in a sealed flask for 5 hours. Excess trimethylamine and ethanol were removed in vacuo.

NMR: δ=0.9 (t, 3H), 1.1–2.0 (m, 38H), 2.39 (t, 2H), 3.15 (m, 2H), 3.46 (s, 9H), 3.5–3.8 (m, 2H), 4.59 (bs, 4H), 4.9 (m, 1H), 5.25 (bs, 2H).

EXAMPLE 15

1-Octadecylaminocarbonyloxy-3-[5-(trimethylammonio)pentanoyloxy]-2-methylenepropane bromide Following the procedure described in Example 14, but replacing 1-octadecylaminocarbonyloxy-3-(6-bromohexanoyloxy)-2-methylenepropane with 1-octadecylaminocarbonyloxy-3-(5-bromopentanoyloxy)-2-methylenepropane (from Preparation 10), the desired product was obtained.

NMR: δ=0.9 (t, 3H), 1.1–2.0 (m, 36H), 2.48 (t, 2H), 3.15 (m, 2H), 3.45 (s, 9H), 3.75 (m, 2H), 4.6 (m, 4H), 4.9 (m, 1H), 5.25 (bs, 2H).

EXAMPLE 16

1-Octadecylaminocarbonyloxy-3-[4-(1-pyridinio)butylaminocarbonyloxy]-2-methylenepropane bromide Following the procedure described in Example 6, but replacing 1-octadecylaminocarbonyloxy-3-(6-bromohexanoyloxy)-2-methylenepropane with 1-octadecylaminocarbonyloxy-3-(4-bromobutylaminocarbonyloxy)-2-methylenepropane (from Preparation 14), the desired product was obtained.

NMR: δ=0.9 (t, 3H), 1.1–1.9 (m, 34H), 1.9–2.3 (m, 2H), 3–3.4 (m, 4H), 4.53 (bs, 4H), 5.0 (m, 2H), 5.17 (bs, 2H), 5.3 (m, 1H), 6.35 (m, 1H), 8.1 (t, 2H), 8.54 (t, 1H), 9.63 (d, 2H).

EXAMPLE 17

1-Octadecylaminocarbonyloxy-3-[2-(1-pyridinio)ethylaminocarbonyloxy]-2-methylenepropane bromide Following the procedure described in Example 6, but replacing 1-octadecylaminocarbonyloxy-3-(6-bromohexanoyloxy)-2-methylenepropane with 1-octadecylaminocarbonyloxy-3-(2-bromoethylaminocarbonyloxy)-2-methylenepropane (from Preparation 15), the desired product was obtained.

NMR: δ=0.9 (t, 3H), 1.1–1.7 (m, 32H), 3.13 (m, 2H), 3.8 (m, 2H), 4.45 (m, 4H), 5.15 (m, 4H), 5.45 (t, 1H), 7.1 (m, 1H), 8.1 (t, 2H), 8.5 (t, 1H), 9.38 (d, 2H).

EXAMPLE 18

1-Octadecylaminocarbonyloxy-3-[4-(trimethylammonio)butylaminocarbonyloxy]-2-methylenepropane bromide Following the procedure described in Example 14, but replacing 1-octadecylaminocarbonyloxy-3-(6-bromohexanoyloxy)-2-methylenepropane with 1-octadecylaminocarbonyloxy-3-(4-bromobutylaminocarbonyloxy)-2-methylenepropane (from Preparation 14), the desired product was obtained.

NMR: δ=0.9 (t, 3H), 1–2 (m, 36H), 3.2 (m, 4H), 3.40 (bs, 9H), 3.74 (m, 2H), 4.56 (bs, 4H), 5.22 (m, 3H), 6.3 (t, 1H).

EXAMPLE 19

1-Octadecylaminocarbonyloxy-3-[2-(trimethylammonio)ethylaminocarbonyloxy]-2-methylenepropane bromide Following the procedure described in Example 14, but replacing 1-octadecylaminocarbonyloxy-3-(6-bromohexanoyloxy)-2-methylenepropane with 1-octadecylaminocarbonyloxy-3-(2-bromoethylaminocarbonyloxy)-2-methylenepropane (from Preparation 15), the desired product was obtained.

NMR: $\delta$=0.9 (t, 3H), 1.1–1.5 (m, 32H), 3.1 (m, 2H), 3.46 (bs, 9H), 3.79 (m, 4H), 4.58 (m, 4H), 5.23 (bs, 2H), 5.25 (m, 1H), 7.1 (m, 1H).

EXAMPLE 20

1-Hexadecyloxy-3-[4-(trimethylammonio)butanoyloxy]-2-methylenepropane bromide

Following the procedure described in Example 14, but replacing 1-octadecylaminocarbonyloxy-3-(6-bromohexanoyloxy)-2-methylenepropane with 1-hexadecyloxy-3-(4-bromobutanoyloxy)-2-methylenepropane (from Preparation 20), the desired product was obtained.

NMR: $\delta$=0.9 (t, 3H), 1.1–1.8 (m, 28H), 2.1 (m, 2H), 2.57 (t, 2H), 3.39 (m, 2H), 3.49 (bs, 9H), 3.75 (m, 2H), 3.96 (bs, 2H), 4.61 (bs, 2H), 5.20 (m, 2H).

EXAMPLE 21

1-Hexadecyloxy-3-[6-(trimethylammonio)hexanoyloxy]-2-methylenepropane

Following the procedure described in Example 14, but replacing 1-octadecylaminocarbonyloxy-3-(6-bromohexanoyloxy)-2-methylenepropane with 1-hexadecyloxy-3-(6-bromohexanoyloxy)-2-methylenepropane (from Preparation 18), the desired product was obtained.

NMR: $\delta$=0.9 (t, 3H), 1.1–2.0 (m, 34H), 2.38 (t, 2H), 3.3–3.7 (m, 4H), 3.46 (bs, 9H), 3.96 (bs, 2H), 4.58 (bs, 2H), 5.19 (m, 2H).

EXAMPLE 22

1-Hexadecyloxy-3-[11-(trimethylammonio)undecanoyloxy)-2-methylenepropane bromide Following the procedure described in Example 14, but replacing 1-octadecylaminocarbonyloxy-3-(6-bromohexanoyloxy)-2-methylenepropane with 1-hexadecyloxy-3-(11-bromoundecanoyloxy)-2-methylenepropane (from Preparation 21), the desired product was obtained.

NMR: $\delta$=0.88 (t, 3H), 1.25 (bs, 38H), 1.3–1.8 (m, 6H), 2.34 (t, 2H), 3.3–3.6 (m, 4H), 3.47 (s, 9H), 3.97 (bs, 2H), 4.59 (bs, 2H), 5.19 (bs, 2H).

EXAMPLE 23

1-Hexadecyloxy-3-(1-pyridinioacetoxy)-2-methylenepropane bromide

1-Hexadecyloxy-3-bromoacetoxy-2-methylenepropane (from Preparation 19) (0.65 g) was dissolved in dry pyridine (20 ml). After 1.5 hours at 22° C. the mixture was evaporated in dryness in vacuo.

NMR: $\delta$=0.87 (t, 3H), 1.25 (bs, 26H), 1.45 (m, 2H), 3.45 (t, 2H), 3.97 (bs, 2H), 4.74 (bs, 2H), 5.25 (bs, 2H), 6.28 (bs, 2H), 8.11 (t, 2H), 8.57 (t, 1H), 9.40 (d, 2H).

EXAMPLE 24

1-Hexadecyloxy-3-[6-(1-pyridinio)hexanoyloxy]-2-methylenepropane bromide

Following the procedure described in Example 6, but replacing 1-octadecylaminocarbonyloxy-3-(6-bromohexanoyloxy)-2-methylenepropane with 1-hexadecyloxy-3-(6-bromohexanoyloxy)-2-methylenepropane (from Preparation 18), the desired product was obtained.

NMR: $\delta$=0.87 (t, 3H), 1.25 (bs, 28H), 1.3–1.5 (m, 4H), 2.1 (m, 2H), 2.36 (m, 2H), 3.39 (m, 2H), 3.95 (bs, 2H), 4.56 (bs, 2H), 5.01 (m, 2H), 5.17 (bd, 2H), 8.16 (m, 2H), 8.56 (m, 1H), 9.50 (d, 2H).

EXAMPLE 25

1-Hexadecyloxy-3-[11-(1-pyridinio)undecanoyloxy]-2-methylenepropane bromide

Following the procedure described in Example 6, but replacing 1-octadecylaminocarbonyloxy-3-(6-bromohexanoyloxy)-2-methylenepropane with 1-hexadecyloxy-3-(11-bromoundecanoyloxy)-2-methylenepropane (from Preparation 21), the desired product was obtained.

NMR: $\delta$=0.87 (t, 3H), 1.2–1.7 (bs, 42H), 2.05 (m, 2H), 2.33 (t, 2H), 3.40 (t, 2H), 3.96 (bs, 2H), 4.59 (bs, 2H), 4.99 (t, 2H), 5.19 (bs, 2H), 8.17 (t, 2H), 8.55 (m, 1H), 9.50 (d, 2H).

EXAMPLE 26

1-Hexadecyloxy-3-[4-(trimethylammonio)butylaminocarbonyloxy]-2-methylenepropane bromide Following the procedure described in Example 14, but replacing 1-octadecylaminocarbonyloxy-3-(6-bromohexanoyloxy)-2-propane with 1-hexadecyloxy-3-(4-bromobutylaminocarbonyloxy)-2-methylenepropane (from Preparation 16), the desired product was obtained.

NMR: $\delta$=0.88 (t, 3H), 1.26 (bs, 28H), 1.70 (m, 4H), 3.30 (m, 4H), 3.41 (m, 9H), 3.73 (t, 2H), 3.96 (bs, 2H), 4.55 (bs, 2H), 5.18 (bs, 2H), 6.00 (bt, 1H).

EXAMPLE 27

1-Hexadecyloxy-3-[2-(trimethylammonio)ethylaminocarbonyloxy]-2-methylenepropane bromide Following the procedure described in Example 14, but replacing 1-octadecylaminocarbonyloxy-3-(6-bromohexanoyloxy)-2-methylenepropane with 1-hexadecyloxy-3-(2-bromoethylaminocarbonyloxy)-2-methylenepropane (from Preparation 17), the desired product was obtained.

NMR: $\delta$=0.88 (t, 3H), 1.25 (bs, 26H), 1.50 (m, 2H), 3.38 (t, 2H), 3.46 (s, 9H), 3.69 (q, 2H), 3.80 (bm, 2H), 3.95 (bs, 2H), 4.57 (bs, 2H), 5.17 (bs, 2H), 6.95 (bt, 1H).

EXAMPLE 28

1-Hexadecyloxy-3-[4-(1-pyridinio)butylaminocarbonyloxy]-2-methylenepropane bromide Following the procedure described in Example 6, but replacing 1-octadecylaminocarbonyloxy-3-(6-bromohexanoyloxy)-2-methylenepropane with 1-hexadecyloxy-3-(4-bromobutylaminocarbonyloxy)-2-methylenepropane (from Preparation 16), the desired product was obtained.

NMR: δ=0.88 (t, 3H), 1.2–1.9 (m, 32H), 3.20 (q, 2H), 3.38 (t, 2H), 3.95 (bs, 2H), 4.54 (bs, 2H), 5.10 (t, 2H), 5.16 (bs, 2H), 5.90 (bt, 1H).

EXAMPLE 29

1-Hexadecyloxy-3-[2-(1-pyridinio)ethylaminocarbonyloxy]-2-methylenepropane bromide Following the procedure described in Example 6, but replacing 1-octadecylaminocarbonyloxy-3-(6-bromohexanoyloxy)-2-methylenepropane with 1-hexadecyloxy-3-(2-bromoethylaminocarbonyloxy)-2-methylenepropane (from Preparation 17), the desired product was obtained.

NMR: δ=0.88 (t, 3H), 1.1–1.7 (m, 28H), 3.36 (t, 2H), 3.85 (q, 2H), 3.89 (bs, 2H), 4.40 (bs, 2H), 5.11 (bs, 2H), 5.22 (t, 2H), 6.85 (bt, 1H), 8.0 (m, 2H), 8.46 (m, 1H), 9.40 (bd, 2H).

EXAMPLE 30

1-Hexadecanoyloxy-3-[6-(1-pyridinio)hexanoyloxy]-2-methylenepropane bromide

Following the procedure described in Example 6, but replacing 1-octadecylaminocarbonyloxy-3-(6-bromohexanoyloxy)-2-methylenepropane with 1-hexadecanoyloxy-3-(6-bromohexanoyloxy)-2-methylenepropane (from Preparation 22), the desired product was obtained.

NMR: δ=0.88 (t, 3H), 1.1–2 (m, 30H), 2.12 (m, 2H), 2.35 (m, 4H), 4.58 (bs, 4H), 5.05 (t, 2H), 5.25 (bs, 2H), 8.15 (t, 2H), 8.55 (t, 1H), 9.58 (d, 2H).

EXAMPLE 31

1-Hexadecanoyloxy-3-[4-(1-pyridinio)butylaminocarbonyloxy]-2-methylenepropane bromide Following the procedure described in Example 6, but replacing 1-octadecylaminocarbonyloxy-3-(6-bromohexanoyloxy)-2-methylenepropane with 1-hexadecanoyloxy-3-(4-bromobutylaminocarbonyloxy)-2-methylenepropane (from Preparation 23), the desired product is obtained.

EXAMPLE 32

1-Hexadecylaminothiocarbonyloxy-3-[6-(1-pyridinio)-hexanoyloxy]-2-methylenepropane bromide Following the procedure described in Example 6, but replacing 1-octadecylaminocarbonyloxy-3-(6-bromohexanoyloxy)-2-methylenepropane with 1-hexadecylaminothiocarbonyloxy-3-(6-bromohexanoyloxy)-2-methylenepropane (from Preparation 24), the desired product was obtained.

NMR: δ=0.88 (t, 3H), 1.25 (s, 28H), 0.9–2.0 (m, 4H), 2.05 (m, 2H), 2.37 (t, 2H), 3.2–3.6 (m, 2H), 4.60 (m, 2H), 4.92 (m, 2H), 4.99 (t, 2H), 5.26 (m, 2H), 6.8–7.6 (m, 1H), 8.16 (t, 2H), 8.56 (t, 1H), 9.57 (d, 2H).

EXAMPLE 33

1-Hexadecyloxycarbonyloxy-3-[6-(1-pyridinio)hexanoyloxyl]-2-methylenepropane bromide Following the procedure described in Example 6, but replacing 1-octadecylaminocarbonyloxy-3-(6-bromohexanoyloxy)-2-methylenepropane with 1-hexadecyloxycarbonyloxy-3-(6-bromohexanoyloxy)-2-methylenepropane (from Preparation 25), the desired product was obtained.

NMR: δ=0.88 (t, 3H), 1.25 (s, 28H), 1.0–2.3 (m, 6H), 2.36 (t, 2H), 4.13 (t, 2H), 4.59 (s, 2H), 4.63 (s, 2H), 5.05 (t, 2H), 5.29 (s, 2H), 8.16 (t, 2H), 8.56 (t, 1H), 9.57 (d, 2H).

EXAMPLE 34

1-Octadecylaminocarbonyloxy-3-[6-(1-pyridinio)hexanoyloxy]-2-isopropylidenepropane bromide Following the procedure described in Example 6, but replacing 1-octadecylaminocarbonyloxy-3-(6-bromohexanoyloxy)-2-methylenepropane with 1-octadecylaminocarbonyloxy-3-(6-bromohexanoyloxy)-2-isopropylidenepropane (from Preparation 27), the desired compound was obtained.

NMR: δ=0.87 (t, 3H), 1.25 (s, 32H), 1.0–2.2 (m, 6H), 1.82 (s, 3H), 1.84 (s, 3H), 2.32 (t, 2H), 3.13 (q, 2H), 4.62 (bs, 2H), 4.64 (bs, 2H), 4.70 (m, 1H), 5.05 (t, 2H), 8.12 (t, 2H), 8.52 (t, 1H), 9.57 (d, 2H).

EXAMPLE 35

1-Octadecylaminocarbonyloxy-3-[6-(1-pyridinio)hexanoyloxy]-2-ethylidenepropane bromide Following the procedure described in Example 6, but replacing 1-octadecylaminocarbonyloxy-3-(6-bromohexanoyloxy)-2-methylenepropane with an approx. 1:1 mixture of E- and Z-isomers of 1-octadecylaminocarbonyloxy-3-(6-bromohexanoyloxy)-2-ethylidenepropane (from Preparation 29), an approx. 1:1 mixture of E- and Z-isomers of the desired compound is obtained.

EXAMPLE 36

1-Hexadecanoyloxy-3-[6-(3-thiazolio)hexanoyloxy]-2-methylenepropane bromide

Following the procedure described in Example 9, but replacing 1-octadecylaminocarbonyloxy-3-(6-bromohexanoyloxy)-2-methylenepropane with 1-hexadecanoyloxy-3-(6-bromohexanoyloxy)-2-methylenepropane (from Preparation 22), the desired products was obtained.

NMR: δ=0.88 (s, 3H), 1.25 (s, 24H), 1.1–2.1 (m, 8H), 2.34 (m, 4H), 4.58 (s, 4H), 4.90 (m, 2H), 5.25 (s, 2H), 8.40 (bs, 1H), 8.64 (bs, 1H), 11.18 (bs, 1H).

EXAMPLE 37

1-Hexadecanoyloxy-3-[8-(1-pyridinio)octanoyloxy]-2-methylenepropane bromide

1-Hexadecanoyloxy-3-(8-bromooctanoyloxy)-2-methylenepropane (from Preparation 30) (0.80 g) was dissolved in dry pyridine (20 ml) and heated to 100° C. for 8 hours. Excess pyridine was removed in vacuo.

NMR: δ=0.88 (t, 3H), 1.25 (s, 30H), 1.1–2.2 (m, 6H), 2.32 (t, 4H), 4.58 (s, 4H), 5.02 (t, 2H), 5.25 (s, 2H), 8.23 (t, 2H), 8.57 (t, 1H), 9.38 (d, 2H).

EXAMPLE 38

1-Octadecylaminocarbonyloxy-3-[8-(1-methyl-3-imidazolio)octanoyloxy]-2-methylenepropane iodide 1-Octadecylaminocarbonyloxy-3-[8-(1-imidazolyl)octanoyloxy]-2-methylenepropane (from Preparation 33) (0.55 g) was dissolved in chloroform (10 ml). Methyl iodide (6 ml) was added, and the mixture stirred at 22° C. for 24 hours. The mixture was evaporated to dryness in vacuo to give the desired product.

NMR: δ=0.88 (t, 3H), 1.25 (s, 34H), 1.0–1.8 (m, 6H), 1.90 (m, 2H), 2.34 (t, 2H), 3.14 (q, 2H), 4.11 (s, 3H), 4.33 (t, 2H), 4.58 (s, 4H), 4.70 (bt, 1H), 5.24 (bs, 2H), 7.45 (m, 1H), 7.52 (m, 1H), 9.96 (s, 1H).

EXAMPLE 39

1-Octadecylaminocarbonyloxy-3-[6-(1-methyl-3-imidazolio)hexanoyloxy]-2-methylenepropane bromide Following the procedure described in Example 38, but replacing 1-octadecylaminocarbonyloxy-3-[8-(1-imidazolyl)octanoyloxy]-2-methylenepropane with 1-octadecylaminocarbonyloxy-3-[6-(1-imidazolyl)hexanoyloxy]-2-methylenepropane (from Preparation 34) the desired product was obtained.

NMR: $\delta=0.88$ (t, 3H), 1.26 (s, 32H), 1.0–2.0 (m, 6H), 2.32 (t, 2H), 3.14 (q, 2H), 4.10 (s, 3H), 4.36 (t, 2H), 4.58 (s, 4H), 4.90 (bt, 1H), 5.24 (s, 2H), 7.55 (m, 2H), 9.88 (bs, 1H).

EXAMPLE 40

1-Octadecylaminocarbonyloxy-3-[7-(1-pyridinio)heptylaminocarbonyloxy]-2-methylenepropane bromide Following the procedure described in Example 37, but replacing 1-hexadecanoyloxy-3-(8-bromooctanoyloxy)-2-methylenepropane with 1-octadecylaminocarbonyloxy-3-(7-bromoheptylaminocarbonyloxy)-2-methylenepropane (from Preparation 36) the desired product was obtained.

NMR: $\delta=0.87$ (t, 3H), 1.25 (s, 32H), 1.0–1.8 (m, 6H), 2.10 (m, 4H), 3.13 (q, 4H), 4.56 (s, 4H), 5.03 (t, 2H), 5.20 (s, 2H), 5.25 (bt, 2H), 8.13 (t, 2H), 8.54 (t, 1H), 9.57 (d, 2H).

EXAMPLE 41

1-Octadecylaminocarbonyloxy-3-[5-(1-pyridinio)pentylaminocarbonyloxy]-2-methylenepropane bromide Following the procedure described in Example 37, but replacing 1-hexadecanoyloxy-3-(8-bromooctanoyloxy)-2-methylenepropane with 1-octanoylaminocarbonyloxy-3-(5-bromopentylaminocarbonyloxy)-2-methylenepropane (from Preparation 35) the desired product was obtained.

NMR: $\delta=0.88$ (t, 3H), 1.25 (s, 30H), 1.0–1.7 (m, 6H), 2.10 (m, 2H), 3.12 (m, 4H), 4.53 (s, 4H), 4.9–5.2 (m, 5H), 5.85 (m, 1H), 8.10 (bt, 2H), 8.51 (bt, 1H), 9.60 (bd, 2H).

EXAMPLE 42

1-Octadecylaminocarbonyloxy-3-[7-(3-thiazolio)heptylaminocarbonyloxy]-2-methylenepropane bromide Following the procedure described in Example 9, but replacing 1-octadecylaminocarbonyloxy-3-(6-bromohexanoyloxy)-2-methylenepropane with 1-octadecylaminocarbonyloxy-3-(7-bromoheptylaminocarbonyloxy)-2-methylenepropane (from Preparation 36) the desired product was obtained NMR: $\delta=0.87$ (t, 3H), 1.25 (s, 34H), 1.0–1.8 (m, 6H), 2.0 (m, 2H), 3.16 (q, 4H), 4.56 (s, 4H), 4.85 (t, 2H), 5.15 (t, 1H), 5.20 (s, 2H), 5.45 (m, 1H), 8.40 (s, 1H), 8.70 (s, 1H), 11.14 (s, 1H).

EXAMPLE 43

1-Octadecylaminocarbonyloxy-3-[5-(3-thiazolio)pentylaminocarbonyloxy]-2-methylenepropane bromide Following the procedure described in Example 9, but replacing 1-octadecylaminocarbonyloxy-3-(6-bromohexanoyloxy)-2-methylenepropane with 1-octadecylaminocarbonyloxy-3-(5-bromopentylaminocarbonyloxy)-2-methylenepropane (from Preparation 35) the desired product was obtained.

NMR: $\delta=0.88$ (t, 3H), 1.25 (s, 32H), 1.1–1.8 (m, 4H), 2.05 (m, 2H), 3.14 (bq, 4H), 4.55 (s, 4H), 4.80 (t, 2H), 5.19 (s, 3H), 5.75 (bs, 1H), 8.30 (bs, 1H), 8.70 (bs, 1H), 11.10 (bs, 1H).

EXAMPLE 44

1-Octadecylaminocarbonyloxy-3-[6-(1-pyridazinio)hexanoyloxy]-2-methylenepropane bromide 1-Octadecylaminocarbonyloxy-3-(6-bromohexanoyloxy)-2-methylenepropane (from Preparation 9) (0.28 g) was dissolved in toluene (5 ml). Pyridazine (0.18 ml) was added, and the mixture was stirred at 64° C. for 20 hours. The mixture was evaporated to dryness in vacuo to give the desired product.

NMR: $\delta=0.87$ (t, 3H), 1.25 (s, 32H), 1.0–1.8 (m, 4H), 2.30 (m, 4H), 3.14 (q, 2H), 4.57 (bs, 4H), 4.8–5.3 (m, 5H), 8.80 (m, 1H), 8.90 (m, 1H), 9.50 (bd, 1H), 10.85 (m, 1H).

EXAMPLE 45

1-Octadecylaminocarbonyloxy-3-[7-(1-pyridinio)heptanoyloxy]-2-methylenepropane bromide Following the procedure described in Example 37, but replacing 1-hexadecanoyloxy-3-(8-bromooctanoyloxy)-2-methylenepropane with 1-octadecylaminocarbonyloxy-3-(7-bromoheptanoyloxy)-2-methylenepropane (from Preparation 31) the desired product was obtained.

NMR: $\delta=0.88$ (t, 3H), 1.26 (s, 32H), 1.0–1.8 (m, 6H), 2.07 (m, 2H), 2.33 (t, 2H), 3.13 (q, 2H), 4.57 (s, 4H), 5.01 (t, 2H), 5.10 (bs, 1H), 5.22 (bs, 2H), 8.15 (t, 2H), 8.54 (t, 1H), 9.56 (d, 2H).

EXAMPLE 46

1-Octadecylaminocarbonyloxy-3-[7-(3-thiazolio)heptanoyloxy]-2-methylenepropane bromide Following the procedure described in Example 9, but replacing 1-octadecylaminocarbonyloxy-3-(6-bromohexanoyloxy)-2-methylenepropane with 1-octadecylaminocarbonyloxy-3-(7-bromoheptanoyloxy)-2-methylenepropane (from Preparation 31) the desired product was obtained.

M.p. 55°–56° C. (from acetone/ether).

Elemental analysis: calculated for $C_{33}H_{59}BrN_2O_4S$, $H_2O$: C 58.47%, H 9.07%, Br 11.79%, N 4.13%, S 4.73%, $H_2O$ 2.65%, found C 58.31%, H 9.01%, Br 11.53%, N 4.18%, S 4.54%, $H_2O$ 2.74%. Hygroscopic.

NMR: $\delta=0.88$ (t, 3H), 1.25 (s, 32H), 1.0–2.0 (m, 6H), 2.10 (m, 2H), 2.35 (t, 2H), 3.14 (q, 2H), 4.58 (s, 4H), 4.88 (t, 2H), 5.02 (m, 1H), 5.24 (s, 2H), 8.43 (m, 1H), 8.69 (d, 1H), 11.15 (s, 1H).

EXAMPLE 47

1-Octadecylaminocarbonyloxy-3-[7-(3-thiazolio)heptanoyloxy]-2-methylenepropane methanesulfate Following the procedure described in Example 9, but replacing 1-octadecylaminocarbonyloxy-3-(6-bromohexanoyloxy)-2-methylenepropane with 1-octadecylaminocarbonyloxy-3-[7-(methanesulfonyloxy)heptanoyloxy]-2-methylenepropane (from Preparation 32), the desired product was obtained.

NMR: $\delta=0.88$ (t, 3H), 1.26 (s, 32H), 1.0–1.8 (m, 6H), 2.0 (m, 2H), 2.33 (t, 2H), 2.76 (t, 3H), 3.16 (q, 2H), 4.58 (s, 4H), 4.70 (t, 2H), 5.0 (t, 1H), 5.23 (s, 2H), 8.35 (m, 1H), 8.43 (m, 1H), 10.72 (bs, 1H).

EXAMPLE 48

1-Pentadecylaminocarbonyloxy-3-[8-(1-pyridinio)octanoyloxy]-2-methylenepropane bromide Following the procedure described in Example 37, but replacing 1-hexadecanoyloxy-3-(8-bromooctanoyloxy)-2-methylenepropane with 1-pentadecylaminocarbonyloxy-3-(8-bromooctanoyloxy)-2-methylenepropane (from Preparation 13), the desired product was obtained.

NMR: $\delta = 0.87$ (s, 3H), 1.25 (s, 28H), 1.1–1.9 (m, 6H), 2.05 (m, 2H), 2.32 (m, 2H), 3.16 (q, 2H), 4.58 (s, 4H), 4.95 (m, 3H), 5.24 (s, 2H), 8.17 (m, 2H), 8.57 (t, 1H), 9.60 (d, 2H).

EXAMPLE 49

1-Pentadecylaminocarbonyloxy-3-[6-(1-pyridinio)hexanoyloxy]-2-methylenepropane bromide Following the procedure described in Example 37, but replacing 1-hexadecanoyloxy-3-(8-bromooctanoyloxy)-2-methylenepropane with 1-pentadecylaminocarbonyloxy-3-(6-bromohexanoyloxy)-2-methylenepropane (from Preparation 12), the desired product was obtained.

NMR: $\delta = 0.87$ (s, 3H), 1.25 (s, 26H), 1.0–1.9 (m, 4H), 2.08 (m, 2H), 2.36 (t, 2H), 3.16 (q, 2H), 4.57 (s, 4H), 5.00 (m, 3H), 5.22 (s, 2H), 8.13 (t, 2H), 8.52 (t, 1H), 9.55 (d, 2H).

EXAMPLE 50

1-Hexadecylaminothiocarbonyloxy-3-[6-(3-thiazolio)hexanoyloxy]-2-methylenepropane bromide Following the procedure described in Example 9, but replacing 1-octadecylaminocarbonyloxy-3-(6-bromohexanoyloxy)-2-methylenepropane with 1-hexadecylaminothiocarbonyloxy-3-(6-bromohexanoyloxy)-2-methylenepropane (from Preparation 24), the desired product was obtained.

NMR: $\delta = 0.87$ (t, 3H), 1.25 (s, 26H), 1.0–2.2 (m, 8H), 2.38 (t, 2H), 3.2–3.7 (m, 2H), 4.61 (bs, 2H), 4.8–5.1 (m, 4H), 5.30 (m, 2H), 11.20 (bs, 1H).

EXAMPLE 51

1-Octadecyloxycarbonyloxy-3-[7-(3-thiazolio)heptanoyloxy]-2-methylenepropane bromide Following the procedure described in Example 9, but replacing 1-octadecylaminocarbonyloxy-3-(6-bromohexanoyloxy)-2-methylenepropane with 1-octadecyloxycarbonyloxy-3-(7-bromoheptanoyloxy)-2-methylenepropane (from Preparation 38), the desired product was obtained.

NMR: $\delta = 0.88$ (t, 3H), 1.26 (s, 32H), 1.0–1.8 (m, 6H), 2.05 (m, 2H), 2.34 (t, 2H), 4.13 (t, 2H), 4.61 (s, 2H), 4.63 (s, 2H), 4.85 (t, 2H), 5.30 (s, 2H), 8.40 (s, 1H), 8.64 (bd, 1H), 11.15 (bs, 1H).

EXAMPLE 52

1-Hexadecyloxycarbonyloxy-3-[8-(1-pyridinio)octanoyloxy]-2-methylenepropane bromide Following the procedure described in Example 37, but replacing 1-hexadecanoyloxy-3-(8-bromooctanoyloxy)-2-methylenepropane with 1-hexadecyloxycarbonyloxy-2-(8-bromooctanoyloxy)-2-methylenepropane (from Preparation 39) the desired product was obtained.

NMR: $\delta = 0.88$ (t, 3H), 1.25 (s, 28H), 1.0–2.0 (m, 8H), 2.10 (m, 2H), 2.33 (t, 2H), 4.13 (t, 2H), 4.60 (s, 2H), 4.63 (s, 2H), 5.03 (t, 2H), 5.29 (s, 2H), 8.17 (t, 2H), 8.57 (t, 1H), 9.58 (d, 2H).

EXAMPLE 53

1-Hexadecyloxycarbonyloxy-3-[8-(3-thiazolio)octanoyloxy]-2-methylenepropane bromide Following the procedure described in Example 9, but replacing 1-octadecylaminocarbonyloxy-3-(6-bromohexanoyloxy)-2-methylenepropane with 1-hexadecyloxycarbonyloxy-3-(8-bromooctanoyloxy)-2-methylenepropane (from Preparation 39) the desired product was obtained.

NMR: $\delta = 0.88$ (t, 3H), 1.25 (s, 28H), 1.0–2.0 (m, 8H), 2.10 (m, 2H), 2.33 (t, 2H), 4.13 (t, 2H), 4.61 (s, 2H), 4.64 (s, 2H), 4.88 (t, 2H), 5.31 (s, 2H), 8.45 (bs, 1H), 8.65 (d, 1H), 11.20 (bs, 1H).

EXAMPLE 54

1-Hexadecyloxycarbonyloxy-3-[6-(3-thiazolio)hexanoyloxy]-2-methylenepropane bromide Following the procedure described in Example 9, but replacing 1-octadecylaminocarbonyloxy-3-(6-bromohexanoyloxy)-2-methylenepropane with 1-hexadecyloxycarbonyloxy-3-(6-bromohexanoyloxy)-2-methylenepropane (from Preparation 25) the desired product was obtained.

NMR: $\delta = 0.88$ (t, 3H), 1.25 (s, 28H), 1.0–2.2 (m, 6H), 2.37 (t, 2H), 4.13 (t, 2H), 4.61 (bs, 4H), 4.90 (t, 2H), 5.31 (bs, 2H), 8.40 (m, 1H), 11.15 (bs, 1H).

EXAMPLE 55

1-Octadecylaminocarbonyloxy-3-[8-(1-pyridinio)octanoyloxy]-2-isopropylidenepropane bromide Following the procedure described in Example 37, but replacing 1-hexadecanoyloxy-3-(8-bromooctanoyloxy)-2-methylenepropane with 1-octadecylaminocarbonyloxy-3-(8-bromooctanoyloxy)-2-isopropylidenepropane (from Preparation 40) the desired product was obtained.

NMR: $\delta = 0.88$ (t, 3H), 1.25 (s, 36H), 1.1–2.2 (m, 6H), 1.82 (s, 3H), 1.84 (s, 3H), 2.27 (t, 2H), 3.13 (q, 2H), 4.63 (bs, 4H), 4.75 (bt, 1H), 5.03 (t, 2H), 8.55 (m, 1H), 9.57 (bd, 2H).

EXAMPLE 56

1-Octadecylaminocarbonyloxy-3-[6-(3-thiazolio)hexanoyloxy]-2-isopropylidenepropane bromide Following the procedure described in Example 9, but replacing 1-octadecylaminocarbonyloxy-3-(6-bromohexanoyloxy)-2-methylenepropane with 1-octadecylaminocarbonyloxy-3-(6-bromohexanoyloxy-2-isopropylidenepropane (from Preparation 27) the desired product was obtained.

NMR: $\delta = 0.87$ (t, 3H), 1.25 (s, 32H), 1.0–2.2 (m, 6H), 1.83 (bs, 6H), 2.33 (t, 2H), 3.13 (q, 2H), 4.63 (bs, 2H), 4.65 (bs, 2H), 4.89 (m, 3H), 8.40 (m, 1H), 8.65 (bd, 1H), 11.16 (bs, 1H).

EXAMPLE 57

1-Octadecylaminocarbonyloxy-3-[8-(3-thiazolio)octanoyloxy]-2-isopropylidenepropane bromide Following the procedure described in Example 9, but replacing 1-octadecylaminocarbonyloxy-3-(6-bromohexanoyloxy)-2-methylenepropane with 1- octadecylaminocarbonyloxy-3-(8-bromooctanoyloxy)-2-isopropylidenepropane (from Preparation 40) the desired product was obtained.

NMR: δ=0.88 (t, 3H), 1.25 (s, 36H), 1.0–2.1 (m, 6H), 1.83 (s, 3H), 1.84 (s, 3H), 2.28 (t, 2H), 3.13 (q, 2H), 4.64 (bs, 2H), 4.66 (bs, 2H), 4.87 (m, 3H), 8.41 (m, 1H), 8.61 (m, 1H), 11.18 (bs, 1H).

EXAMPLE 58

1-Pentadecylaminocarbonyloxy-3-[6-(1-pyridinio)hexanoyloxy]-2-isopropylidene bromide Following the procedure described in Example 37, but replacing 1-hexadecanoyloxy-3-(8-bromooctanoyloxy)-2-methylenepropane with 1-pentadecylaminocarbonyloxy-3-(6-bromohexanoyloxy)-2-methylenepropane (from Preparation 43) the desired product was obtained.

NMR: δ=0.87 (t, 3H), 1.25 (s, 26H), 1.1–2.2 (m, 6H), 1.82 (s, 3H), 1.84 (s, 3H), 2.32 (t, 2H), 3.15 (q, 2H), 4.63 (s, 2H), 4.65 (s, 2H), 4.8 (bs, 1H), 5.05 (t, 2H), 8.12 (t, 2H), 8.50 (m, 1H), 9.57 (d, 2H).

EXAMPLE 59

1-Pentadecylaminocarbonyloxy-3-[8-(1-pyridinio)octanoyloxy]-2-isopropylidenepropane bromide Following the procedure described in Example 37, but replacing 1-hexadecanoyloxy-3-(8-bromooctanoyloxy)-2-methylenepropane with pentadecylaminocarbonyloxy-3-(8-bromooctanoyloxy)-2-isopropylidenepropane (from Preparation 42) the desired product was obtained.

NMR: δ=0.88 (t, 3H), 1.25 (s, 30H), 1.2–2.1 (m, 6H), 1.82 (s, 3H), 1.84 (s, 3H), 2.28 (t, 2H), 3.13 (q, 2H), 4.65 (bs, 4H), 4.70 (m, 1H), 5.03 (t, 2H), 8.15 (t, 2H), 8.55 (t, 1H), 9.55 (d, 2H).

EXAMPLE 60

1-Pentadecylaminocarbonyloxy-3-[6-(3-thiazolio)hexanoyloxy]-2-isopropylidenepropane bromide Following the procedure described in Example 9, but replacing 1-octadecylaminocarbonyloxy-3-(6-bromohexanoyloxy)-2-methylenepropane with 1-pentadecylaminocarbonyloxy-3-(6-bromohexanoyloxy)-2-isopropylidenepropane (from Preparation 43) the desired product was obtained.

NMR: δ=0.88 (t, 3H), 1.26 (s, 26H), 1.1–2.2 (m, 6H), 1.82 (s, 3H), 1.84 (s, 3H), 2.32 (t, 2H), 3.14 (q, 2H), 4.65 (s, 4H), 4.88 (m, 3H), 8.41 (m, 1H), 8.66 (m, 1H), 11.16 (bs, 1H).

EXAMPLE 61

1-Pentadecylaminocarbonyloxy-3-[8-(3-thiazolio)octanoyloxy]-2-isopropylidenepropane bromide Following the procedure described in Example 9, but replacing 1-octadecylaminocarbonyloxy-3-(6-bromohexanoyloxy)-2-methylenepropane with 1-pentadecylaminocarbonyloxy-3-(8-bromooctanoyloxy)-2-isopropylidenepropane (from Preparation 42) the desired product was obtained.

NMR: δ=0.88 (t, 3H), 1.25 (s, 30H), 1.0–2.2 (m, 6H), 1.83 (s, 3H), 1.84 (s, 3H), 2.32 (t, 2H), 3.14 (q, 2H), 4.65 (bs, 4H), 4.88 (m, 3H), 8.42 (m, 1H), 8.62 (m, 1H), 11.17 (bs, 1H).

EXAMPLE 62

1-Tridecylaminocarbonyloxy-(3-[6-(1-pyridinio)hexanoyloxy]-2-methylenepropane bromide Following the procedure described in Example 37, but replacing 1-hexadecanoyloxy-3-(8-bromooctanoyloxy)-2-methylenepropane with 1-tridecylaminocarbonyloxy-3-(6-bromohexanoyloxy)-2-methylenepropane from Preparation 45) the desired product was obtained.

NMR: δ=0.88 (t, 3H), 1.25 (s, 20H), 1.0–2.0 (m, 6H), 2.15 (bt, 2H), 2.36 (t, 2H), 3.16 (q, 2H), 4.57 (s, 4H), 5.04 (m, 3H), 5.23 (bs, 2H), 8.17 (t, 2H), 8.58 (t, 1H), 9.65 (d, 2H).

EXAMPLE 63

1-Pentadecylaminocarbonyloxy-3-[6-(3-thiazolio)hexyloxy]-2-methylenepropane methanesulfonate Following the procedure described in Example 9, but replacing 1-octadecylaminocarbonyloxy-3-(6-bromohexanoyloxy)-2-methylenepropane with 1-pentadecylaminocarbonyloxy-3-[6-(methanesulfonyloxy)hexyloxy]-2-methylenepropane (from Preparation 57) the desired product was obtained.

NMR: δ=0.88 (t, 3H), 1.26 (s, 26H), 1.1–1.7 (m, 6H), 2.0 (m, 2H), 2.77 (bs, 3H), 3.15 (q, 2H), 3.38 (t, 2H), 3.94 (s, 2H), 4.56 (s, 2H), 4.70 (t, 2H), 5.07 (s, 1H), 5.17 (s, 2H), 8.45 (m, 2H), 10.80 (bs, 1H).

EXAMPLE 64

1-Pentadecylaminocarbonyloxy-3-[6-(1-pyridinio)hexyloxy]-2-methylenepropane methanesulfonate Following the procedure described in Example 37, but replacing 1-hexadecanoyloxy-3-(8-bromooctanoyloxy)-2-methylenepropane with 1-pentadecylaminocarbonyloxy-3-[6-(methanesulfonyloxy)hexyloxy]-2-methylenepropane (from Preparation 57) the desired product was obtained.

NMR: δ=0,87 (t, 3H), 1.25 (bs, 26H), 1.0–1.8 (m, 6H), 2.0 (m, 2H), 2.73 (s, 3H), 3.14 (q, 2H), 3.38 (t, 2H), 3.94 (s, 2H), 4.55 (s, 2H), 4.79 (t, 2H), 5.05 (bs, 1H), 5.15 (s, 2H), 8.11 (t, 2H), 8.49 (t, 1H), 9.20 (d, 2H).

EXAMPLE 65

1-Octadecylaminocarbonyloxy-3-[6-(3-thiazolio)hexyloxy]-2-methylenepropane methanesulfonate Following the procedure described in Example 9, but replacing 1-octadecylaminocarbonyloxy-3-(6-bromohexanoyloxy)-2-methylenepropane with 1-octadecylaminocarbonyloxy-3-[6-(methanesulfonyloxy)hexyloxy]-2-methylenepropane (from Preparation 58) the desired product was obtained.

NMR: δ=0.87 (t, 3H), 1.25 (bs, 38H), 2.0 (bm, 2H), 2.77 (s, 3H), 3.15 (q, 2H), 3.38 (t, 2H), 3.95 (s, 2H), 4.57 (s, 2H), 4.70 (t, 2H), 5.10 (s, 1H), 5.16 (s, 2H), 8.40 (m, 2H), 10.76 (bs, 1H).

EXAMPLE 66

1-Octadecylaminocarbonyloxy-3-[6-(1-pyridinio)hexyloxy]-2-methylenepropane methanesulfonate Following the procedure described in Example 37, but replacing 1-hexadecanoyloxy-3-(8-bromooctanoyloxy)-2-methylenepropane with 1-octadecylaminocarbonyloxy-3-[6-(methanesulfonyloxy)hexyloxy]-2-methylenepropane (from Preparation 58) the desired product was obtained.

NMR: δ=0.87 (t, 3H), 1.25 (s, 32H), 1.1–1.7 (m, 6H), 2.0 (m, 2H), 2.75 bs, 3H), 3.15 (q, 2H), 3.38 (t, 2H), 3.94 (s, 2H), 4.56 (s, 2H), 4.80 (t, 2H), 5.05 (bs, 1H), 5.16 (s, 2H), 8.08 (t, 2H), 8.45 (t, 1H), 9.22 (d, 2H).

EXAMPLE 67

1-Octadecyloxycarbonyloxy-3-[6-(3-thiazolio)hexyloxy]-2-methylenepropane methanesulfonate Following the procedure described in Example 9, but replacing 1-octadecylaminocarbonyloxy-3-(6-bromohexanoyloxy)-2-methylenepropane with 1-octadecyloxycarbonyloxy-3-[6-(methanesulfonyloxy)-hexyloxy]-2-methylenepropane (from Preparation 56) the desired product was obtained.

NMR: δ=0.87 (s, 3H), 1.26 (s, 32H), 1.0–2.1 (m, 8H), 2.76 (bs, 3H), 3.38 (t, 2H), 3.96 (s, 2H), 4.13 (t, 2H), 4.62 (s, 2H), 4.70 (t, 2H), 5.22 (s, 2H), 8.35 (bs, 2H), 10.80 (s, 1H).

EXAMPLE 68

1-Octadecyloxycarbonyloxy-3-[6-(1-pyridinio)hexyloxy]-2-methylenepropane methanesulfonate Following the procedure described in Example 37, but replacing 1-hexadecanoyloxy-3-(8-bromooctanoyloxy)-2-methylenepropane with 1-octadecyloxycarbonyloxy-3-[6-(methanesulfonyloxy)hexyloxy]-2-methylenepropane (from Preparation 56) the desired product was obtained.

NMR: δ=0.87 (s, 3H), 1.26 (s, 32H), 1.1–2.1 (m, 8H), 2.75 (s, 3H), 3.37 (t, 2H), 3.95 (s, 2H), 4.12 (t, 2H), 4.62 (s, 2H), 4.80 (t, 2H), 5.21 (s, 2H), 8.10 (m, 2H), 8.50 (m, 1H), 9.31 (d, 2H).

EXAMPLE 69

1-Hexadecyloxycarbonyloxy-3-[6-(3-thiazolio)hexyloxy]-2-methylenepropane methanesulfonate Following the procedure described in Example 9, but replacing 1-octadecylaminocarbonyloxy-3-(6-bromohexanoyloxy)-2-methylenepropane with 1-hexadecyloxycarbonyloxy-3-[6-(methanesulfonyloxy)hexyloxy]-2-methylenepropane (from Preparation 55), the desired product was obtained.

NMR: δ=0.88 (t, 3H), 1.26 (s, 28H), 1.1–2.0 (m, 8H), 2.77 (s, 3H), 3.39 (t, 2H), 3.96 (s, 2H), 4.13 (t, 2H), 4.63 (s, 2H), 4.70 (t, 2H), 5.22 (s, 2H), 8.31 (s, 2H), 10.82 (s, 1H).

EXAMPLE 70

1-Hexadecyloxycarbonyloxy-3-[6-(1-pyridinio)hexyloxy]-2-methylenepropane methanesulfonate Following the procedure described in Example 37, but replacing 1-hexadecanoyloxy-3-(8-bromooctanoyloxy)-2-methylenepropane with 1-hexadecyloxycarbonyloxy-3-[6-(methanesulfonyloxy)hexyloxy]-2-methylenepropane (from Preparation 55) the desired product was obtained.

NMR: δ=0.87 (t, 3H), 1.25 (s, 28H), 1.1–1.9 (m, 6H), 2.05 (m, 2H), 2.75 (s, 3H), 3.37 (t, 2H), 3.95 (s, 2H), 4.12 (t, 2H), 4.62 (s, 2H), 4.82 (t, 2H), 5.22 (s, 2H), 8.09 (t, 2H), 8.47 (t, 1H), 9.25 (d, 2H).

EXAMPLE 71

1-Octadecyloxycarbonyloxy-3-[1-(pyridinio)heptanoyloxy]-2-methylenepropane bromide Following the procedure described in Preparation 37, but replacing 1-hexadecanoyloxy-3-(8-bromooctanoyloxy)-2-methylenepropane with 1-octadecyloxycarbonyloxy-3-(7-bromoheptanoyloxy)-2-methylenepropane (from Preparation 38), the desired product was obtained.

NMR: δ=0.88 (t, 3H), 1.25 (s, 32H), 1.0–1.8 (m, 6H), 2.10 (m, 2H), 2.33 (t, 2H), 4.13 (t, 2H), 4.60 (s, 2H), 4.63 (s, 2H), 5.04 (t, 2H), 5.29 (s, 2H), 8.15 (m, 2H), 8.55 (m, 1H), 9.57 (d, 2H).

EXAMPLE 72

1-Octadecylaminocarbonyloxy-3-[6-(1-quinolinio)hexanoyloxy]-2-methylene propane bromide Following the procedure described in Preparation 6, but replacing pyridine with quinoline, the desired product is obtained.

EXAMPLE 73

1-Octadecylaminocarbonyloxy-3-[6-(3-chloro-1-pyridinio)hexanoyloxy]-2-methylenepropane bromide Following the procedure described in Preparation 9, but replacing thiazole with 3-chloropyridine, the desired product is obtained.

EXAMPLE 74

1-Octadecylaminocarbonyloxy-3-[7-(3-thiazolio)heptanoyloxy]-2-methylenepropane 4-toluenesulfonate 1-Octadecylaminocarbonyloxy-3-[7-(3-thiazolio)heptanoyloxy]-2-methylenepropane bromide (from Example 46) (0.25 g) was dissolved in 0.1M sodium 4-toluenesulfonate (50 ml) and passed through a column of Amberlite ® XAD-7 (20–50 mesh, 15 ml). The column was washed with 0.1M sodium 4-(toluenesulfonate (15 ml) followed by water (45 ml). Nitrogen was passed through the column which finally was eluted with methanol (50 ml). The methanol eluate was evaporated to dryness in vacuo, and the desired product was obtained.

EXAMPLE 75

1-Octadecylaminocarbonyloxy-3-[7-(3-thiazolio)heptanoyloxy]-2-methylenepropane chloride Following the procedure described in Example 74, but replacing sodium 4-toluenesulfonate with sodium chloride, the desired product is obtained.

EXAMPLE 76

1-Octadecylaminocarbonyloxy-3-[7-(3-thiazolio)heptanoyloxy]-2-methylenepropane iodide Following the procedure described in Example 74, but replacing sodium 4-toluenesulfonate with sodium iodide, the desired product is obtained.

EXAMPLE 77

| Aerosol | |
|---|---|
| 1-Octadecylaminocarbonyloxy-3-[7-(3-thiazolio)heptanoyloxy]-2-methylenepropane bromide (GS-1160-180) (active substance) | 1,000 mg |
| Water for injections to make | 1,000 ml |

The active substance is dissolved in a suitable amount of water for injections by gentle heating. Water for injections is added to make a final volume of 1,000 ml.

The solution is filtered through a sterile 0.2 μm membranefilter and filled aseptically into suitable single dose containers, each containing 5 ml. One dose of 5 ml (equal to 5 mg active substance) is inhaled by means of a suitable nebulizer.

EXAMPLE 78

| Capsule | |
|---|---|
| GS-1160-180 (active substance) | 50 g |
| Gactose fine crystalline | 300 g |
| Magnesium stearate | 3 g |

The active substance is mixed in a suitable mixer with lactose until a homogeneous state is reached. The magnesium stearate is added, and the blending procedure is continued for a few minutes. By means of a suitable capsule-filling machine hard gelatine capsules size 0 are filled, each with 353 mg of the mixture.

EXAMPLE 79

| Tablet | |
|---|---|
| GS-1160-180 (active substance) | 100 g |
| Lactose | 200 g |
| Starch | 100 g |
| Methylcellulose | 4 g |
| Magnesium stearate | 4 g |

The active substance, lactose and starch are mixed to a homogeneous state in a suitable mixer and moistened with a 5 percent aqueous solution of methylcellulose 15 cps. The mixing is continued until granules are formed. If necessary, the wet granulation is passed through a suitable screen and dried to a water content of less than 2.5% in a suitable dryer, e.g. fluid bed or drying oven. The dried granulation is passed through a 1 mm screen. Magnesium stearate is added, and the mixing is continued for a short period of time.

Tablets with a weight of 408 mg are produced from the granulation by means of a suitable tabletting machine.

EXAMPLE 80

| Suppository | |
|---|---|
| GS-1160-180 (active substance) | 200 g |
| Suppository base, Witepsol W-35 | 1,900 g |

Cocoa butter is slowly heated to form a melt not exceeding 60° C. The active substance is added to the melt, and suppositories with a weight of 2.1 grams are prepared by moulding.

EXAMPLE 81

| Topical formulation | | |
|---|---|---|
| I | GS-1160-180 (active substance) | 20 g |
| | Cetostearyl alcohol | 100 g |
| | Liquid paraffin | 100 g |
| | White soft paraffin | 50 g |
| | Polyoxyethylene sorbitane monostearate | 50 g |
| II | Methylparaben | 2 g |
| | Glycerol | 100 g |
| | Water to make | 1,000 g |

The ingredients stated under I are melted together and heated to 70° C. in a vessel fitted with stirrer and homogenizer. In another vessel, the water phase (II) is prepared by heating to 70° C. The water phase is slowly added to the oil phase with continuous stirring and homogenization.

The active substance is added, and the temperature is kept for 15 minutes at 70° C. The vessel is cooled to 40° C. under continuous stirring and homogenization. The cooling is continued to a temperature below 25° C. under slow stirring.

EXAMPLE 82

| Formulation for injection | |
|---|---|
| GS-1160-180 (active substance) | 10 g |
| Ethanol | 100 g |
| Propylene glycol | 200 g |
| Water for injection to make | 1,000 ml |

The active substance is dissolved in a mixture of ethanol and propylene glycol by slight heating. Water for injection is added to a final volume of 1,000 ml. The injection solution is sterile filtered through a 0.2 μm membranefilter and filled aseptically into ampoules, each containing 5 ml.

EXAMPLE 83

| Ophthalmic solution | |
|---|---|
| GS-1160-180 (active substance) | 2 g |
| Mannitol | 50 g |
| Hydroxyethylcellulose | 5 g |
| Phenyl ethyl alcohol | 5 g |
| Water for injection to make | 5 g |
| | 1,000 g |

A 2 percent concentrate of hydroxyethylcellulose in water for injection including phenyl ethyl alcohol is prepared by slowly spreading the cellulose on the water surface. The concentrate is allowed to stand for complete swelling of the cellulose.

The active substance and mannitol are dissolved in the remaining amount of water of injection.

The solutions are carefully mixed together and sterilized. Under aseptic conditions the solution is filled into suitable sterile containers.

What we claim is:

1. A compound of the formula I

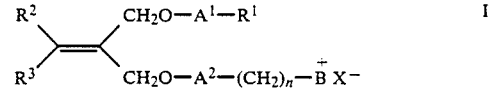

where O—$A^1$ and O—$A^2$, which can be the same or different, each represents O, O—C(O), O—C(O)NH, O—C(S)NH or O—C(O)O, $R^1$ represents an alkyl or alkenyl group of 10–22 carbon atoms, n is an integer from 1 to 11, $B^+$ represents $N^+$(Het), where —$N^+$(Het) stands for 1-pyridinio, 1-pyridazinio, 1-pyrimidinio, 1-pyrazinio, 3-oxazolio, 3-thiazolio, 1-isoquinolinio, 1-quinolinio, 3-alkyl-1-imid-azolio; $X^-$ means the anion of a pharmaceutically acceptable inorganic or organic acid; and $R^2$ and $R^3$ are the same or different, and represent hydrogen or alkyl groups of 1–4 carbon atoms.

2. A compound according to claim 1, in crystalline form.

3. A compound according to claim 1, in which $X^-$ stands for the anion of an inorganic acid selected from the group consisting of hydrochloric acid, hydrobromic acid, hydriodic acid, sulfuric acid, phosphoric acid, and nitric acid, or for the anion of an organic acid selected from the group consisting of acetic acid, lactic acid, tartaric acid, benzoic acid, citric acid, methanesulfonic acid, ethanesulfonic acid, benzenesulfonic acid, toluenesulfonic acid, and isethionic acid, $X^-$ standing in particular for chloride, bromide, iodide, or the anions of methanesulfonic acid or p-toluenesulfonic acid.

4. A compound according to claim 1, in which $R^2$ and $R^3$ are both hydrogen, and n is an integer from 4 to 9.

5. A compound according to claim 1, selected from the group consisting of 1-octadecylaminocarbonyloxy-3-[7-(3-thiazolio)heptanoyloxy]-2-methylenepropane bromide, 1-octadecylaminocarbonyloxy-3-[6-(1-pyridinio)hexanoyloxy]-2-methylenepropane bromide, 1-pentadecylaminocarbonyloxy-3-[8-(3-thiazolio)octanoyloxy]-2-methylenepropane bromide, 1-hexadecyloxycarbonyloxy-3-[8-(3-thiazolio)octanoyloxy]-2-methylenepropane bromide, 1-pentadecylaminocarbonyloxy-3-[8-(3-thiazolio)octanoyloxy]-2-isopropylidenepropane bromide, 1-octadecylaminocarbonyloxy-3-[5-(1-pyridinio)pentylaminocarbonyloxy]-2-methylenepropane bromide, 1-octadecylaminocarbonyloxy-3-[6-(3-thiazolio)hexyloxy]-2-methylenepropane methanesulfonate.

6. A compound according to claim 1 where $-N^+(-Het)$ is 3-thiazolio.

7. A compound according to claim 6 which is 1-octadecylaminocarbonyloxy-3-[7-(3-thiazolio)heptanoyloxy]-2-methylenepropane bromide.

8. A pharmaceutical composition for use in inhibiting the effect of platelet activating factor comprising an effective amount of a compound according to claim 1, together with pharmaceutically acceptable, non-toxic carriers and/or auxiliary agents.

9. A pharmaceutical composition according to claim 8, in parenteral form.

10. A pharmaceutical composition according to claim 8, in topical form.

11. A pharmaceutical composition according to claim 8, in enteral form.

12. A method for inhibiting the effect of platelet activating factor in a host in need of such inhibiting effect which comprises administering to said host an effective amount of a compound according to claim 1.

* * * * *